(12) United States Patent
Gilbert

(10) Patent No.: US 10,213,542 B2
(45) Date of Patent: Feb. 26, 2019

(54) SYSTEMS AND METHODS FOR FLOW STAGNATION CONTROL

(71) Applicant: Asia Pacific Medical Technology Development Company, Ltd, Central (HK)

(72) Inventor: John R. Gilbert, Brookline, MA (US)

(73) Assignee: Asia Pacific Medical Technology Development Company, Ltd, Central, Hong Kong (CN)

( * ) Notice: Subject to any disclaimer, the term of this patent is extended or adjusted under 35 U.S.C. 154(b) by 182 days.

(21) Appl. No.: 14/932,382

(22) Filed: Nov. 4, 2015

(65) Prior Publication Data

US 2017/0119950 A1    May 4, 2017

(51) Int. Cl.
*A61M 1/36* (2006.01)
*A61M 1/10* (2006.01)
(Continued)

(52) U.S. Cl.
CPC ........ *A61M 1/3672* (2013.01); *A61M 1/1006* (2014.02); *A61M 1/1086* (2013.01); *A61M 1/3639* (2013.01); *A61M 1/3653* (2013.01); *A61M 1/3656* (2014.02); *A61M 5/1723* (2013.01); *A61M 25/0075* (2013.01);
(Continued)

(58) Field of Classification Search
CPC .............. A61M 1/3672; A61M 1/3656; A61M 1/1086; A61M 1/1006; A61M 1/3653; A61M 1/3639; A61M 5/1723; A61M 25/0075; A61M 25/10; A61M 2205/3344; A61M 1/3666; A61M 2005/1726; A61M 2025/105; A61M 1/3621; A61M 1/3663; A61M 1/3669; A61M 5/16831; A61M 5/16836; A61M 5/16854
See application file for complete search history.

(56) References Cited

U.S. PATENT DOCUMENTS

| | | |
|---|---|---|
| 4,006,736 A | 2/1977 | Kranys et al. |
| 5,092,339 A | 3/1992 | Geddes et al. |

(Continued)

FOREIGN PATENT DOCUMENTS

| | | |
|---|---|---|
| WO | 1996022117 A2 | 7/1996 |
| WO | 2006132571 A1 | 12/2006 |

(Continued)

OTHER PUBLICATIONS

International Search Report and Written Opinion issued in International Application No. PCT/US2015/058972, dated Jan. 29, 2016.
(Continued)

*Primary Examiner* — Bhisma Mehta
*Assistant Examiner* — Hamza A Darb
(74) *Attorney, Agent, or Firm* — McCarter & English, LLP; Kia L. Freeman; Thomas F. Foley

(57) ABSTRACT

The present disclosure describes flow stagnation control components that allow improved flow control in systems including injection members, while also limiting the creation of regions of little to no flow in the vasculature, resulting in low flow zones or dead zones. The flow stagnation control components can be formed as an imposed minimum conductance component or a controlled flow partitioning system.

11 Claims, 26 Drawing Sheets

(51) Int. Cl.
*A61M 25/10* (2013.01)
*A61M 25/00* (2006.01)
*A61M 5/172* (2006.01)

(52) U.S. Cl.
CPC .......... *A61M 25/10* (2013.01); *A61M 1/3666* (2013.01); *A61M 2005/1726* (2013.01); *A61M 2025/105* (2013.01); *A61M 2205/3344* (2013.01)

(56) References Cited

U.S. PATENT DOCUMENTS

| | | | |
|---|---|---|---|
| 5,788,647 | A | 8/1998 | Eggers |
| 6,167,765 | B1 | 1/2001 | Weitzel |
| 6,287,608 | B1 | 9/2001 | Levin et al. |
| 6,508,777 | B1 | 1/2003 | Macoviak et al. |
| 6,605,106 | B2 | 8/2003 | Schwartz |
| 6,620,188 | B1 | 9/2003 | Ginsburg et al. |
| 6,780,322 | B1 | 8/2004 | Bissler et al. |
| 7,135,008 | B2 | 11/2006 | O'Mahony et al. |
| 7,204,798 | B2 | 4/2007 | Zdeblick et al. |
| 7,771,460 | B2 | 8/2010 | Ginsburg et al. |
| 8,246,669 | B2 | 8/2012 | Machold et al. |
| 9,814,824 | B2 | 11/2017 | Gilbert et al. |
| 2001/0039441 | A1 | 11/2001 | Ash |
| 2004/0073161 | A1 | 4/2004 | Tachibana |
| 2005/0119597 | A1 | 6/2005 | O'Mahony et al. |
| 2006/0167398 | A1* | 7/2006 | Solar .......... A61F 7/12 604/6.13 |
| 2006/0184093 | A1 | 8/2006 | Phipps et al. |
| 2006/0195135 | A1 | 8/2006 | Ayoub |
| 2007/0137296 | A1 | 6/2007 | Krivitski et al. |
| 2007/0161914 | A1 | 7/2007 | Zdeblick et al. |
| 2008/0275377 | A1 | 11/2008 | Paolini et al. |
| 2012/0130298 | A1 | 5/2012 | Demers et al. |
| 2013/0053825 | A1 | 2/2013 | Moulton et al. |
| 2014/0052224 | A1 | 2/2014 | Kassab et al. |
| 2014/0207060 | A1* | 7/2014 | Hochareon ......... A61M 1/3615 604/96.01 |
| 2014/0249386 | A1 | 9/2014 | Caron et al. |
| 2014/0276376 | A1 | 9/2014 | Rohde et al. |
| 2015/0182114 | A1 | 7/2015 | Wang et al. |

FOREIGN PATENT DOCUMENTS

| | | |
|---|---|---|
| WO | PCT/US2015/058972 | 11/2015 |
| WO | PCT/US2015/058982 | 11/2015 |
| WO | PCT/US2015/058985 | 11/2015 |

OTHER PUBLICATIONS

International Search Report and Written Opinion for International Application No. PCT/US15/58982, dated Jan. 12, 2016.
International Search Report and Written Opinion for International Application No. PCT/US15/58985, dated Jan. 14, 2016.
Wood et al., "Elevated plasma free drug concentrations of propanolol and diazepam during cardiac catheterization", Ciculation, 62(5):1119-1122 (1980).
Herzog, E., "Therapeutic hypothermia for cardiac arrest", Live Well New York (2015) (retrieved from http://livewellnewyork.com/articles/treating-cardiac-arrest-gets-cooler).
McKean, S., "Induced moderate hypothermia after cardiac arrest", AACN Advanced Critical Care, 20(4):343-355 (2009).
U.S. Appl. No. 14/932,419, filed Nov. 4, 2015.
U.S. Appl. No. 14/932,414, filed Nov. 4, 2015.

\* cited by examiner

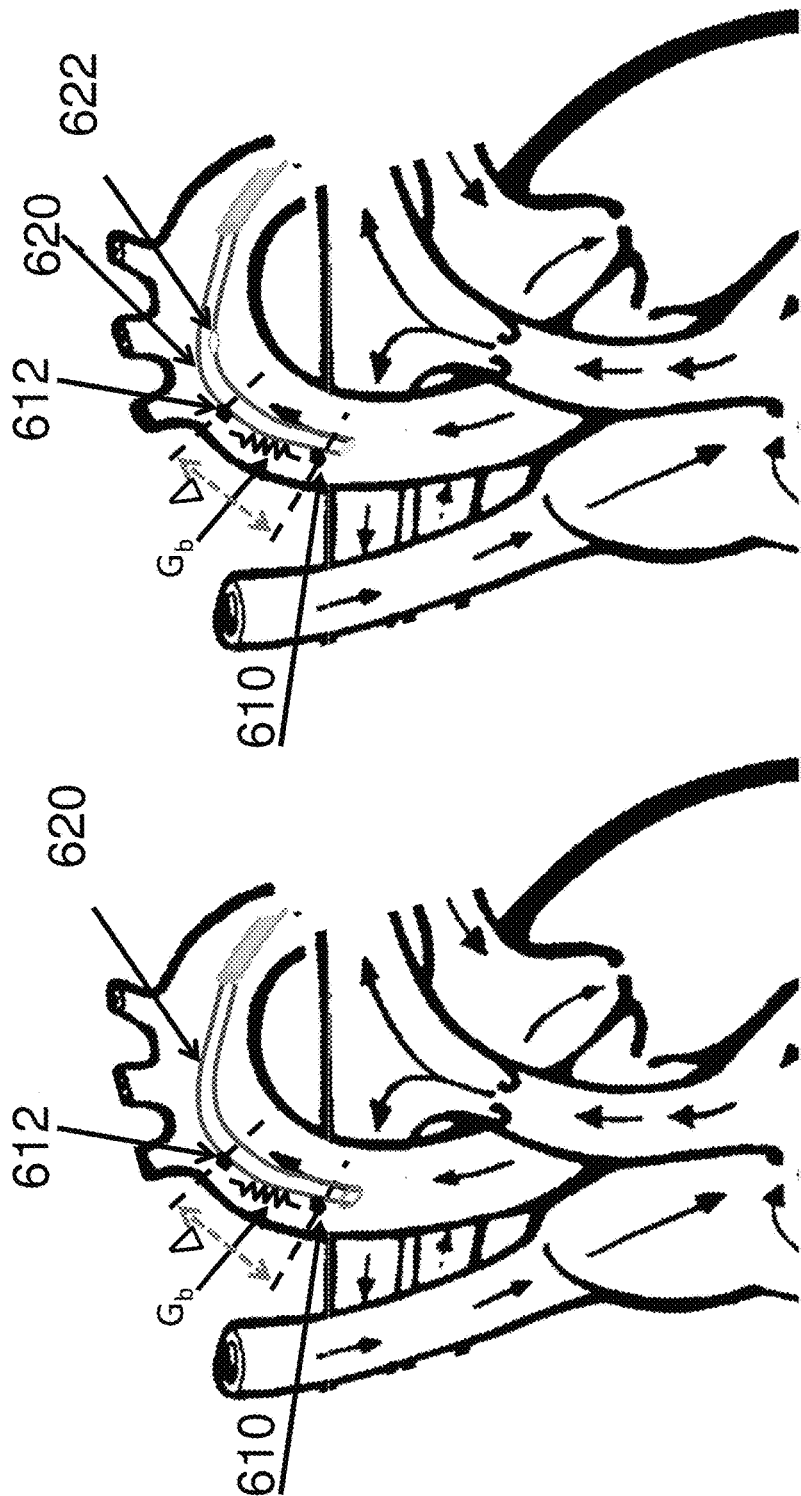

SYSTEMS AND METHODS FOR FLOW STAGNATION CONTROL

BACKGROUND

In design of intravascular catheters, occlusion devices are often used to control or block flow in an artery or vein. However, under some circumstances, occluding the flow in an artery or vein creates a zone of stopped or no-flow region where blood does not move (i.e., also referred to as "dead zones"). In some cases the prolonged creation of a dead zone in blood flow may enhance the risk of creating a thrombus or blood clot, which may be associated with increased risk of patient embolism.

SUMMARY

This instant disclosure provides example systems, devices, apparatus and methods that allow for control of the flow of blood in a portion of an artery or vein, to control the occurrence and duration in time of low-flow or no-flow regions, including dead zones, in a portion of the vasculature. In particular, the example systems, methods, devices, and apparatus allow for control of flow stagnation through use of an imposed minimum conductance component or a controlled flow partitioning system.

In an example, the systems, devices, apparatus and methods use an imposed minimum conductance member coupled to a catheter, injector member, or other instrument, to control the flow rate of the flow of blood in an artery or vein, to control the occurrence and duration in time of the low-flow or no-flow regions, including dead-zones.

In an example, the systems, devices, apparatus and methods are configured to compute values of the conductance of the portion of the vasculature around a portion of the catheter, injector member, or other instrument, based on sensor measurements of at least two pressure sensors coupled to the catheter, injector member, or other instrument, and to control the occurrence and duration in time of the low-flow or no-flow regions, including dead-zones, based on the computed values of conductance.

Example systems, devices, and apparatus can include an extracorporeal circuit and an imposed minimum conductance component. The extracorporeal circuit includes a flow port for returning blood from the extracorporeal circuit to a vasculature of a region of a body and at least one injector member configured to cause blood to flow at a vascular injection point. The at least one injector member includes a lumen and a distal tip. The imposed minimum conductance component is disposed proximate to the distal tip of the at least one injector member.

Example systems, devices, and apparatus can be configured to implement a method using an imposed minimum conductance member. The method includes coupling an extracorporeal circuit to a portion of a body. The extracorporeal circuit includes a flow port for returning blood from the extracorporeal circuit to a vasculature of a region of a body, and at least one injector member configured to cause blood to flow at a vascular injection point. The at least one injector member includes a lumen and a distal tip. An imposed minimum conductance component is disposed proximate to the distal tip of the at least one injector member. The method further includes causing an injected flow from the at least one injector member at a flow rate such that a net or averaged back flow or forward flow is maintained in the vasculature exterior to the at least one injector member above a predetermined minimum flow rate.

Example systems, devices, and apparatus can include an extracorporeal circuit and a controlled flow partitioning system. The extracorporeal circuit includes a flow port for returning blood from the extracorporeal circuit to a vasculature of a region of a body, and an injector member configured to cause blood to flow at a vascular injection point. The at least one injector member includes a lumen and a distal tip. The controlled flow partitioning system includes a first pressure sensor for measuring a first parameter indicative of flow proximate to a distal tip of the injector member, a second pressure sensor for measuring a second parameter indicative of flow, the second sensor being disposed proximate to the injector member at a pre-defined separation proximal from the distal tip, and an injection flow rate source coupled to the extracorporeal circuit, to cause injection flow at a predetermined flow rate pattern at the vascular injection point.

Example systems, devices, and apparatus can be configured to implement a method using a controlled partitioning flow system. The method includes coupling an extracorporeal circuit to a portion of a body. The extracorporeal circuit includes a flow port to return blood from the extracorporeal circuit to a vasculature at a region of a body, and an injector member coupled to the flow port. The injector member includes a distal tip and a shaft having a lumen. The controlled partitioning flow system includes at least a first pressure sensor disposed proximate to the distal tip, at least a second pressure sensor disposed on an outer surface of the shaft of the injector member, and an injection flow rate source coupled to the injection member to control a flow of fluid from the distal tip of the injector member. The method includes controlling the flow of fluid injected at the distal tip of the injector member, using the injection flow rate source, to a predetermined flow rate pattern over a time interval T, recording measurements of pressure using the first pressure sensor and second pressure sensor over the time interval T, and computing at least one of a proximal exterior conductance or a distal exterior conductance at the distal tip of the injector member using data indicative of the measurements of pressure, and the predetermined flow rate pattern.

Example systems, devices, and apparatus can include an extracorporeal circuit, a controlled flow partitioning system, and a console. The extracorporeal circuit can include a flow port for returning blood from the extracorporeal circuit to a vasculature at a region of a body, and an injector member including a distal tip. The controlled flow partitioning system includes a first pressure sensor disposed proximate to the distal tip of the at least one injector member, a second pressure sensor disposed at an outer surface of the at least one injector member, at a predetermined separation proximal from the distal tip, and an injection flow rate source coupled to the injection member to control the flow rate of fluid from the distal tip to a predetermined flow rate pattern. The console includes at least one processing unit programmed to receive data indicative of measurements of pressure using the first pressure sensor and the second pressure sensor over a time interval T with the flow of blood injected at the distal tip at the predetermined flow rate pattern, and compute at least one of a proximal exterior conductance or a distal exterior conductance at the distal tip of the at least one injector member using data indicative of the measurements of pressure and the predetermined flow rate pattern.

Example systems, devices, and apparatus can be configured to implement a method including an extracorporeal circuit. The extracorporeal circuit includes a flow port to return blood from the extracorporeal circuit to a vasculature at a region of a body, an injector member coupled to the flow port, the injector member comprising a distal tip and a shaft having a lumen, at least a first pressure sensor disposed proximate to the distal tip, at least a second pressure sensor disposed on an outer surface of the shaft of the injector member, and an injection flow rate source coupled to the injection member to control a flow of fluid from the distal tip of the injector member. The method includes coupling the extracorporeal circuit to a portion of a body, controlling the flow of fluid injected at the distal tip of the injector member, using the injection flow rate source, to a predetermined flow rate pattern over a first time interval $T_1$, recording measurements of pressure using the first pressure sensor and second pressure sensor over the first time interval $T_1$, computing a value of a proximal exterior conductance at the distal tip of the injector member using data indicative of the measurements of pressure and the predetermined flow rate pattern, calculating the exterior flow rate using the first and second pressure measurements and the computed proximal exterior conductance and using that to calculate the ratio of injected to exterior flow rates in the distal mixed fluid, and controlling the amount of drug or pharmacological agent added to the injected fluid and adjusting that amount using the calculated ratio of injected to exterior flow rates in order to achieve a specified concentration of drug or pharmacological agent in the mixed distal fluid.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

One of ordinary skill in the art will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 6C shows an example catheter coupled to pressure sensors, according to principles of the present disclosure.

FIG. 6D shows another example catheter coupled to pressure sensors, according to principles of the present disclosure.

DETAILED DESCRIPTION

Figure 1A:
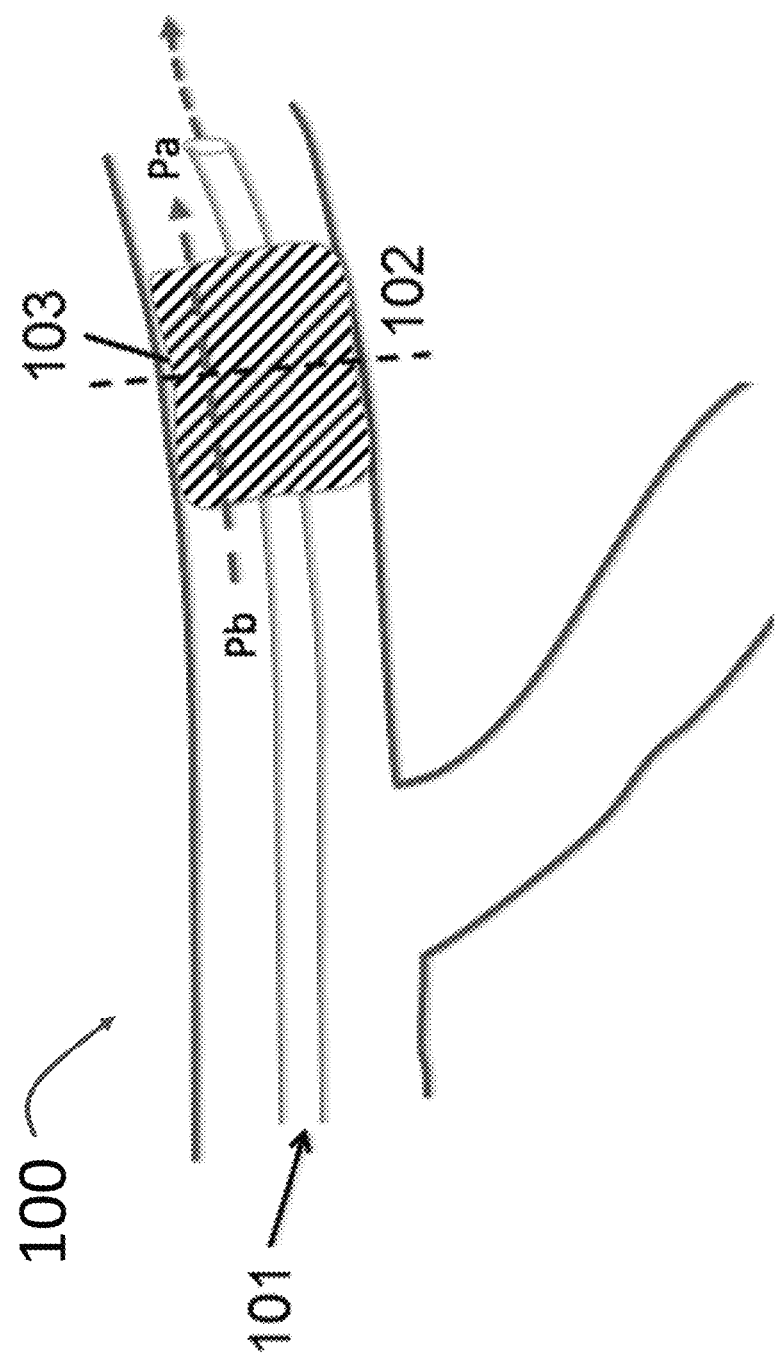
FIG. 1A shows a schematic of an example catheter system, according to principles of the present disclosure.

Following below are more detailed descriptions of various concepts related to, and embodiments of, systems, devices, apparatus and methods that allow for control the flow of blood in a portion of an artery or vein, to control the occurrence of, and duration in time, of low-flow or no-flow regions, including dead-zones, in a portion of the vasculature. Example systems, methods, devices and apparatus are also described that allow for control of at least two zones of selective thermal therapy. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

With respect to surfaces described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a surface or layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the surface, and each other.

The terms "disposed on" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

As used herein, the term "proximal" refers to a direction towards a portion of a catheter, an injector member, or other instrument that a user would operate, such as but not limited to a grip or other handle. As used herein, the term "distal" refers to a direction away from the grip or other handle of the catheter, injector member, or other instrument. For example the tip of the injector member is disposed at a distal portion of the injector member.

During certain procedures using a catheter, blood flow a vein or an artery may be occluded. Whenever blood flow is at least partially blocked, no-flow or low-flow regions, including dead-zones, can arise in portions of the vasculature. For example, intravascular catheters or other similar devices can include occlusion devices for controlling or blocking flow in an artery or vein. Under certain circumstances, occluding the flow of blood in an artery or vein can create zones of significantly diminished blood flow, or no-flow region, where the blood is substantially stagnant. These zones are referred to herein as "dead zones" or "no-flow zones" Tissue may become starved of blood flow, and possibly be compromised, if the no-flow or low-flow region (including dead-zone) persists for lengthy periods of time. In some cases, the prolonged creation of a dead zone in blood flow may enhance the risk of creating a thrombus or blood clot, which is associated with increased risk of an embolism in a patient. The question of arises as to how to minimize these risks from the blockage.

In some systems, the risk of cutoff of blood flow to the tissue fed by an artery is addressed by adding bypass or perfusion lumens, such as described in U.S. Pat. Nos. 5,046,503 and 5,176,638.

The present disclosure describes various example systems, methods, and apparatus for controlling the flow of blood in a portion of an artery or vein, to control the occurrence and duration in time of low-flow or no-flow regions in a portion of the vasculature. As a non-limiting example, the systems, devices, apparatus and methods can be used to control the occurrence and time duration in time of dead-zone regions in a portion of the vasculature In some examples, systems, methods, and apparatus are described for controlling (including reducing) flow stagnation during use of intravascular catheters or other similar devices. Example systems, apparatus, and methods are described for controlling or reducing the occurrence of no-flow or low-flow zones in the vasculature based on data indicative of the conductance of regions of the vasculature. The control of flow stagnation can be achieved using at least one imposed minimum conductance component or using a controlled flow partitioning system. An example imposed minimum conductance component can be used to impose a desired, known value of conductance in regions of the vasculature. If the conductance outside the injector member is known, the fluid injection level at the injection member can be controlled such that there is an amount of fluid flow to flush in an area that would normally form a no-flow or low-flow zone (including a dead zone). An example controlled flow partitioning system can use sensor measurements to compute the conductance in a region of the vasculature, thereby providing a known value of conductance. That is, either of these systems of methodologies can be used to provide a known value of conductance exterior to the catheter member. With these known values of conductance, the fluid flow can be controlled to ensure that either no no-flow or low-flow zones occur in the vasculature, or the duration of time of occurrence of the no no-flow or low-flow zones does not result in damage to tissue or other damage.

Reducing the occurrence of flow stagnation reduces or eliminates the possibility of dead zones or no-flow zones forming in portions of the vasculature.

According to some example implementations, the flow stagnation control can be achieved through use of a controlled flow partitioning system. The controlled flow partitioning system includes components for measuring both the proximal exterior conductance and the distal exterior conductance. The measurements to prevent dead-flow zones in the region proximal to an injector member by modifying the flow injected at the injection member. The example devices, systems, and methods can be operated passively to measure fluid flow, or can be used actively to measure fluid flow through introduction or withdrawal of an amount of fluid.

The present disclosure describes devices, systems, and methods that can be operated actively to prevent or reduce the occurrence of (including to flush) a dead zone that can form in a portion of the vasculature proximate to the catheter during operation.

The term "imposed minimum conductance component" is used herein to refer to a component that controls the reduction of the flow rate in a vasculature segment, while ensuring that the flow rate does not go below a certain minimum value based on an imposed minimum conductance level. Conductance herein is the inverse of resistance. In various examples, the minimum conductance level can be used to control the flow to a fixed value of flow rate (referred to herein as a "fixed-constant"), or as an averaged value of flow rate over a time cycle t that is small as compared to the length of time T of a procedure, i.e., where $t \ll T$ (referred to herein as a "fixed-average"). For example, the time cycle t can be on the order of a heartbeat or minutes, while time period T can be the time of an operation or other procedure, lasting one or more hours.

According to some example embodiments, the flow stagnation control can be achieved through use of the imposed minimum conductance components and systems that are configured to allow improved flow control in extracorporeal blood return. The present disclosure also provides various example imposed minimum conductance components that limit or prevent the formation of dead zones in a region of the artery or vein proximate to the imposed minimum conductance components, and also provides specific dead zone flushing devices or sub-systems.

As used herein, an "injector member" is a device or component that includes a lumen. In an example, the lumen can be used for injecting fluid into the vasculature, either as part of an independent catheter system, or as a component of an example extracorporeal circuit system that is used to inject blood into the vasculature at a specific location in the body.

As used herein, the term "vasculature injection point" refers to the most distal location in the vasculature, away from a catheter entry or vascular puncture location, at which blood is injected into the body.

As used herein, the term "peripheral placed loop" refers to an example extracorporeal circuit that has blood output (from body to circuit) and blood input (from circuit to body) catheters (or other an input flow port and/or output flow port member) that can be placed in contact with a portion of the vasculature of the body, without detailed guidance from fluoroscopy or any other equivalent systems that is normally used to steer devices past arterial or venous branches. This is a subset of all possible placements, some through the peripheral circulation and some through the central circulation.

The term "peripheral" is used herein differently than used in referring to a peripheral circulation system. For example, the catheters (or other an input flow port and/or output flow port member) may be placed in contact with the vena cava, or low into the descending aorta or iliac artery, without using fluoroscopy. These are sometimes considered part of the central system, rather than the peripheral circulation system.

As used herein, the term "systemic perfusion system" refers to a system that couples to blood in the heart via an injector member coupled directly to the main venous feeds to the heart, such as the vena cava (inferior vena cava or superior vena cava), or iliac vein.

As used herein, the term "local perfusion system" refers to a system that has an injector member placed such that a dominant fraction (more than about 50%) of the blood injected feeds to an organ system before returning through the general circulation to the heart.

As used herein, the term "proximal exterior conductance" means the conductance in the space exterior to the device, i.e. between the device and the vascular wall, along a region proximal to the injection member tip.

As used herein, the term "distal exterior conductance" means the total conductance from the site of injection at the tip of an injection member into the distal vasculature. For injection members on the arterial side of the vasculature, this is the conductance from the tip to the venous side of the circulation.

As used herein, the term "controlled flow partitioning system" is a system for measuring or computing values for either or both the proximal exterior conductance and the distal exterior conductance, which then uses those measurements to prevent dead-flow zones in the region proximal to an injection member by modifying the flow rate injected at the injection member. Such a system, as used herein is composed of at least two pressure sensors and a displacement or flow rate controlling pump on the extracorporeal circuit side of the injector member directly controlling flow rate through the injector member. In any example herein, the controlled flow partitioning system can include a distributed array of pressure sensors.

As used herein, the term "flow rate pattern" refers to a functional form of flow rates over a set period of time. For example, the flow of fluid can be set at a fluid flow rate source such that the fluid flow follows the values set by the flow rate pattern. In various examples, the flow rate pattern can be a specified functional form, such as but not limited to a sinusoidal functional form, a sawtooth functional form, a step-function functional form, or another periodic functional form in the art (including more complex functional forms). In other examples, where the flow rate pattern has an irregular functional form, the value of flow rate can be measured at regular time intervals over a specified period of time to provide an approximation of the irregular functional form.

In non-limiting example herein, an imposed minimum conductance component can be configured to set a known, specified proximal conductance around a distal region of an injection member. That proximal conductance can prevent the formation of any no-flow or dead-flow zones. As another example, in a controlled flow partitioning system according to the principles herein, the conductance that is present in the proximal exterior of an injection member is measured (instead of that conductance being created) and that measurement is used to control the flow rate and flushing of relevant zones (including any no-flow or dead-flow zones).

In an example herein, a "biased valve" refers to a component in the wall of a catheter segment between an internal lumen and the outside of the shaft which is exposed to the vasculature. In an example, the "biased value" can be configured such that, if the pressure inside the lumen is larger than the pressure outside the shaft, there is a value of conductance $G_{forward}$ established across the valve. In another example, the "biased valve" can be configured such that, if the pressure inside the lumen is smaller than the pressure outside the shaft, there is a value conductance $G_{backward}$ established across the valve. In an example, the reasonable pressure differences between the lumen and the vasculature can be expressed as $G_{forward} \gg G_{backward}$, or $G_{backward}$ is very small or near zero.

FIG. 1A shows a schematic of an example catheter system 100 that includes a shaft 101 of a device that is disposed in a portion of the vasculature. FIG. 1A also shows a plane 102 through an occlusion component 103 that is mounted on the shaft 101 and is part of the device. The shaft holding device 101 may include a lumen that passes through the device. In an example catheter system 100, the occlusion component 103 may include a balloon that is inflated using saline or other solution. Another example occlusion component 103 may include a membrane that is expanded to press against the arterial wall using the force exerted by a spring or other mechanical actuation. In an example, the occlusion component 103 can be configured to extend from the shaft device 101 of the catheter system 100 to touch and seal against the walls of the artery or vein, to significantly reduce or prevent flow. As shown in FIG. 1A, the example plane 102 is perpendicular to the vascular section. The example occlusion component 103 is used according to the principles herein to modify the fluid flow across plane 102. The fluid flow relates to the flow outside of the base holding shaft. The degree of flow is driven by a difference in pressure between the region before the occlusion component 103 (Pb) and the region after (Pa).

Figure 1C:
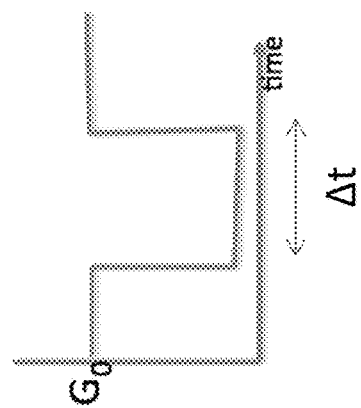
FIGS. 1B-1C show example plots of the fluid conductance in the vascular space across the boundary.
Figure 1B:
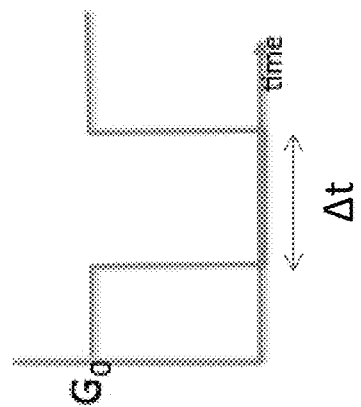

FIGS. 1B and 1C show example graphs of the fluid conductance ($G_0$) versus time in the vascular space across the plane 102 through the occlusion component 103. FIG. 1B shows the fluid conductance ($G_0$) versus time for a full occlusion achieved using occlusion component 103. In the example of FIG. 1B, the fluidic conductance is reduced during the time period Δt when the occlusion component is activated to fully occlude the vascular space. The plot of FIG. 1B shows that fluid conductance goes to zero when the occlusion component 103 is activated for full occlusion. This definition is independent of the pressure gradient/difference (F=G(Pa−Pb)). The plot of FIG. 1C depicts the conditions for the fluid conductance ($G_0$) versus time during a controlled partial occlusion, where an occlusion component according to the principles herein is activated during a time period Δt. As shown in FIG. 1C, the conductance does not go to zero but rather goes to a minimum conductance level that has magnitude greater than zero.

A catheter can be deployed in a wide variety of target locations in the vasculature. However, it is very difficult to precisely control the diameter of the vasculature at the target location. If there is no occlusion element or the occlusion element is not deployed, the leakage flow may be large, and the leakage flow may then prevent optimal control of the forward (distal region) fluid flow. This is subject to the restriction that the flow is larger in larger diameter arteries, and smaller if the artery is smaller. On the other hand a full occlusion can cause a dead zone to form. According to the principles herein, a small controlled leakage flow structure can be used with the occlusion component, so that the dead zone is flushed but the leakage is limited so that it does not distort the valuable control of distal flow from use of the device. For a flow rate similar to blood flow in the carotid or femoral arteries a forward flow rate of 200-500 ml/min would be very useful but a flushing flow rate of 20-50 ml/min or even less can be adequate to flush the dead zone.

As described herein, the minimum conductance level can be a fixed-constant or a fixed-average value. For the fixed-constant, the fluid conductance $G_0$ is constant over time. For the fixed-average, the minimum conductance can be time-varying on a time scale t that is small as compared to the time of overall device activation. In an example, a biased valve can be configured to achieve the controlled partial occlusion such that the conductance varies over a heartbeat. In this example, "fixed-average" refers to a fluid conductance that varies in value during the time cycle of a heartbeat, but that has a non-zero averaged value over that heartbeat. This leads to a non-zero averaged fluid conductance over longer time periods.

In an example, the imposed minimum conductance is achieved in a fixed-constant form. An imposed minimum conductance component located at the distal tip of an extracorporeal injection member is configured to maintain a minimal conductance that provides a flow of fluid to flush the dead-zone that would otherwise be created by any complete occlusion. The size in flow resistance terms of that minimal conductance is set such that the flushing flow is not more than about 50%, or preferably not more than about 10%, of the flow the device being used to direct through the injector member.

In an example, the imposed minimum conductance is achieved in a passive form. An example occlusion element is configured to include an alternative fluidic bypass pathway, allowing a bypass flow to flush the dead-zone that would otherwise be created by the occlusion. The size in flow resistance terms of that bypass is set such that the bypass flow is not more than about 50%, or preferably not more than about 10%, of the flow the device being used to direct through the injector member.

In some examples, the occlusion component can include soft balloons to be used for the occlusions. In an example, the soft balloons may partially be inflated, leading to some leakage conductance. This can be useful since the vasculature is uneven and the amount of leakage conductance with a partial inflation is not observable to the user and/or controllable.

Figure 2A:
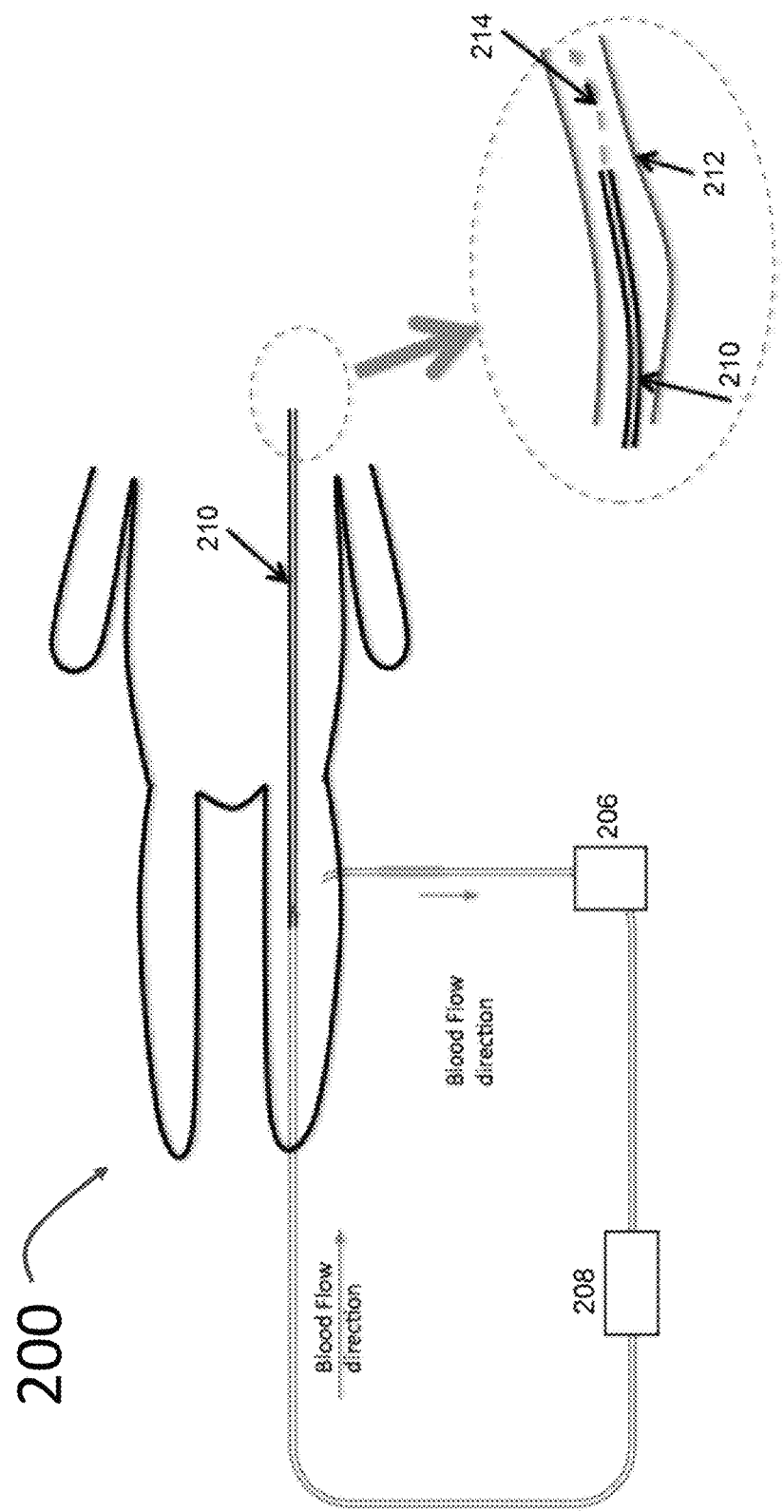
FIG. 2A shows an example extracorporeal circuit, according to principles of the present disclosure.

FIG. 2A shows a schematic of an example extracorporeal circuit 200 that is coupled to an individual. The example extracorporeal circuit 200 includes a pump system 206, a heat exchanger 208, and an injector member 210. An example extracorporeal circuit can include two connections to the vasculature of a patient. Such an example extracorporeal circuit can be implemented to pump blood from the vasculature using one connection and returns blood to the vasculature using the other connection. An example extracorporeal circuit can be used where the heart is inoperative or not supplying sufficient blood flow, or may be used to modify blood and return to systemic flow or to a local region. Other modifications may include oxygenation, dialysis, thermal, removal of bacterial contaminants, removal of cancer causing cells, and others. FIG. 2A shows the injector member 210 coupled to the vasculature of the body of an individual at vascular injection point 212, to return blood 214 to the body based on a flow rate modulated using pump system 206. The most distal location in the vasculature at which blood is injected into the body is referred to herein as the "vasculature injection point".

In one example, the injector member 210 can include an occlusion component to separate blood flow on one side from fluid injected by an extracorporeal circuit through the device shaft on the other side. This can create a zone of no flow or limited flow in a portion of the vasculature, i.e., a dead zone. The dead zone can be avoided if an occlusion system is sited at an exact position relative to the nearest vasculature branch, but it is not possible to guarantee such an exact placement in practice in real patients. As a result, a dead zone is usually formed in the branch including the injection point where blood does not flow. This can potentially cause thrombus or blood clots to form if the occlusion is left in place for long periods of time. Extracorporeal blood supply circuits can be used for long periods of time, such as but not limited to time on the order of hours to days, which can be sufficient time to increase the risk of formation of thrombus or blood clots.

Figure 2B:
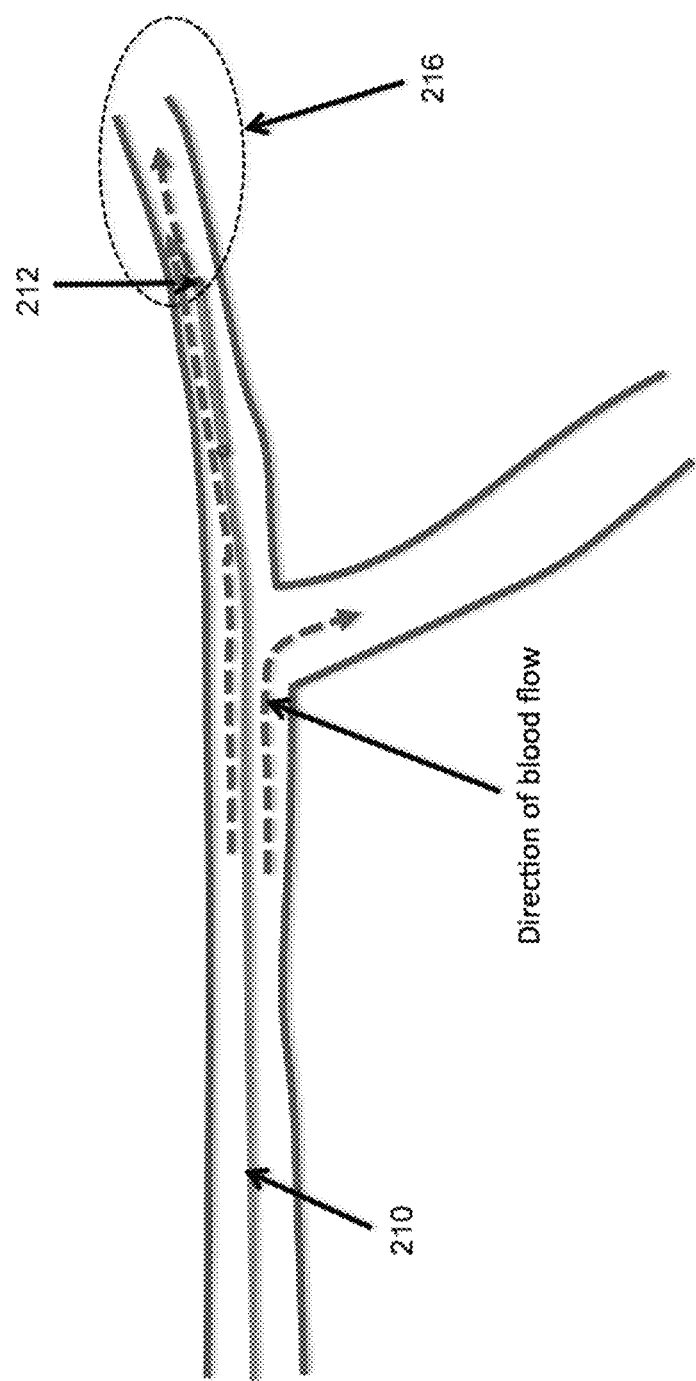
FIGS. 2B-2C show schematics of another catheter system, according to principles of the present disclosure.

FIG. 2B shows an example injector member 210 that is a component of the example extracorporeal circuit system of FIG. 2A that returns blood to a specific location in the body vascular injection point 212. Injecting fluid 216 through shaft lumen can add to blood flow in this branch. To the extent that alternative blood flow is blocked, the injected blood may dominate the flow in the distal vasculature.

Figure 2C:
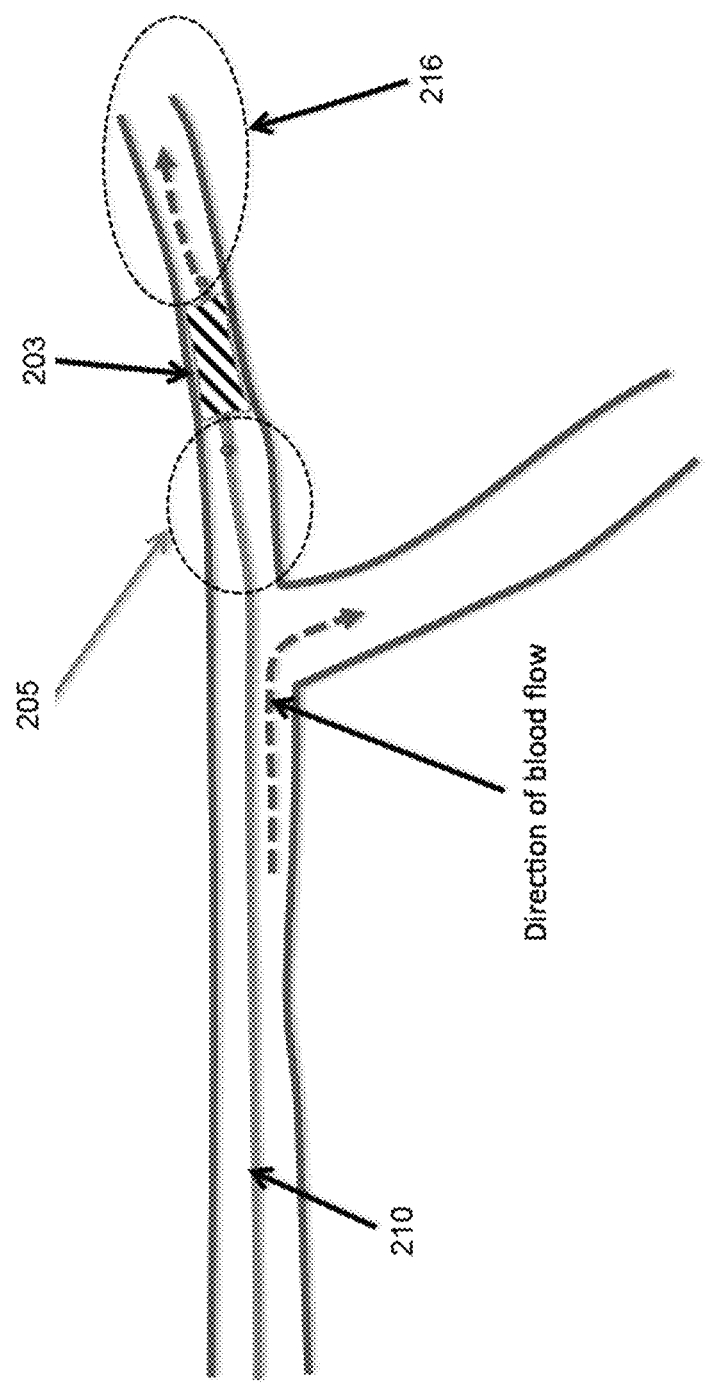

FIG. 2C shows an example injector member 210 that is a component of the example extracorporeal circuit system of FIG. 2A that returns blood (injecting fluid 216) to a specific location in the body. The injector member 210 is coupled to an occlusion component 203 that is shown to fully occlude a portion of the vasculature. As shown in FIG. 2C, when the injector member 210 injects blood at a vascular injection point through the occlusion device 203, a dead zone 205 can form proximate to the occlusion component 203.

Figure 3A:
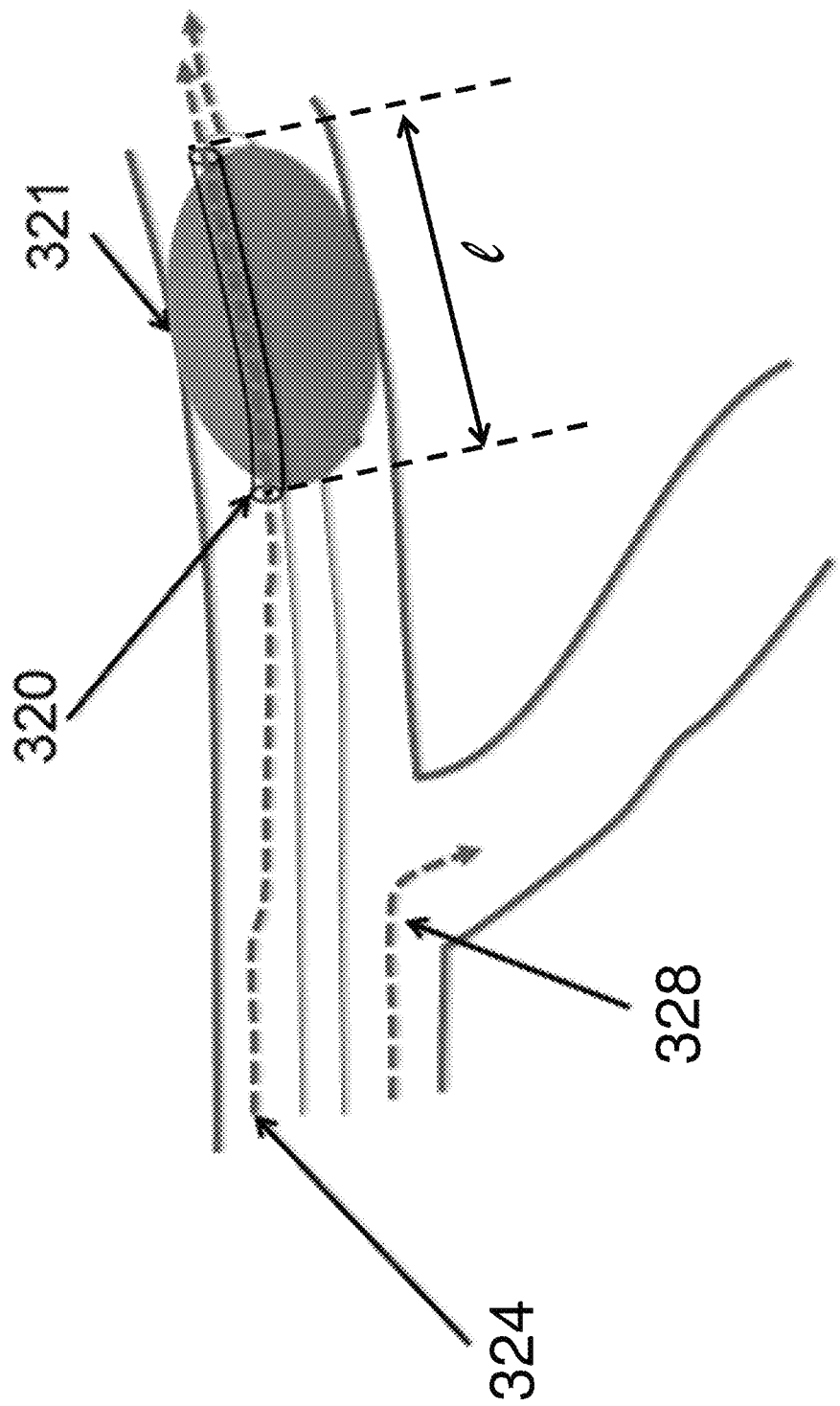
FIGS. 3A-3B show examples of another catheter system, according to principles of the present disclosure.
Figure 3B:
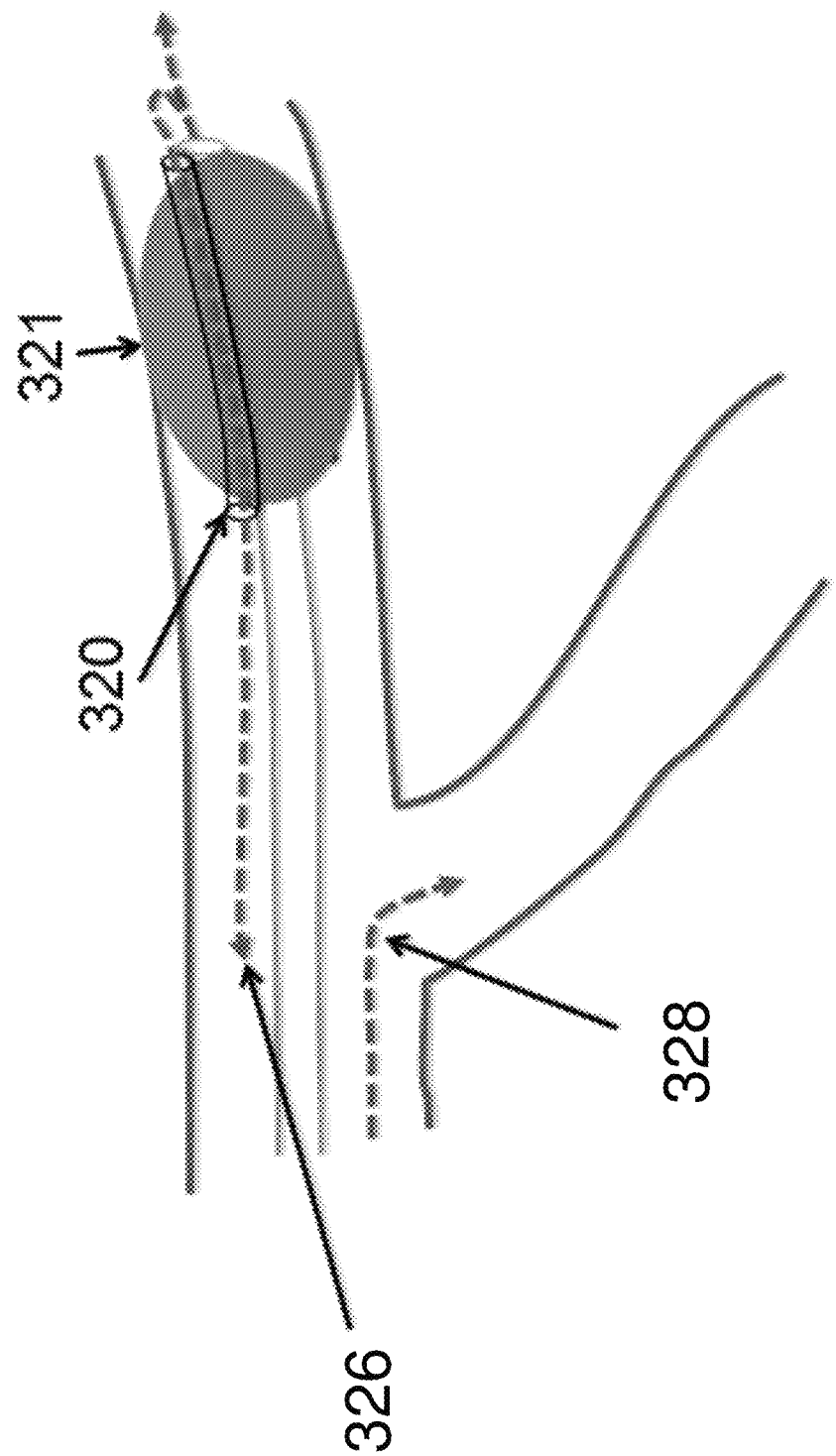

FIGS. 3A-3B show example imposed minimum conductance systems according to the principles herein. The imposed minimum conductance system of FIG. 3A includes a lumen 320, having a discrete length l, that is disposed along the shaft of the device and under a component 321 (such as but not limited to a soft balloon 321), so that it provides a minimum conductance for flow to flush the dead zone. Such a lumen 320 controlled by the design length and the diameter can present a constant flow rate for the fluid and therefore allows a small bypass flow. FIG. 3A shows the forward direction of new flushing flow 324 through lumen 320. FIG. 3B shows the backward direction of flushing flow 326 (flushing flow retrograde) through lumen 320. Dashed lines in FIGS. 3A-3B are used to show the direction of blood flow 328. In both FIG. 3A and FIG. 3B, fluid flowing through the minimal conductance can serve to flush the dead zone proximate to the component 321, thereby preventing or minimizing unwanted thrombus formation.

Figure 4A:
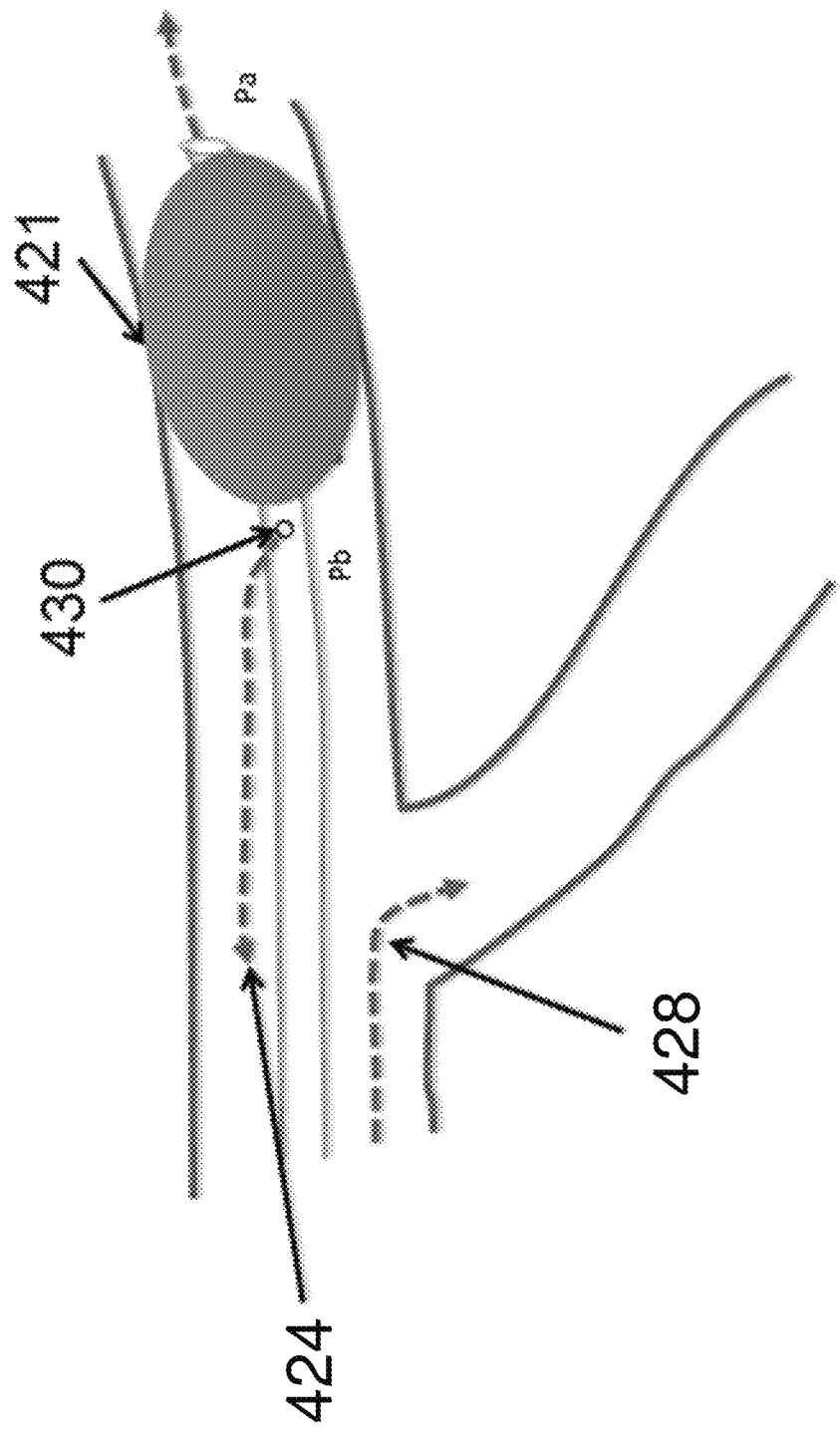
FIGS. 4A-4B show examples of another catheter system, according to principles of the present disclosure.
Figure 4B:
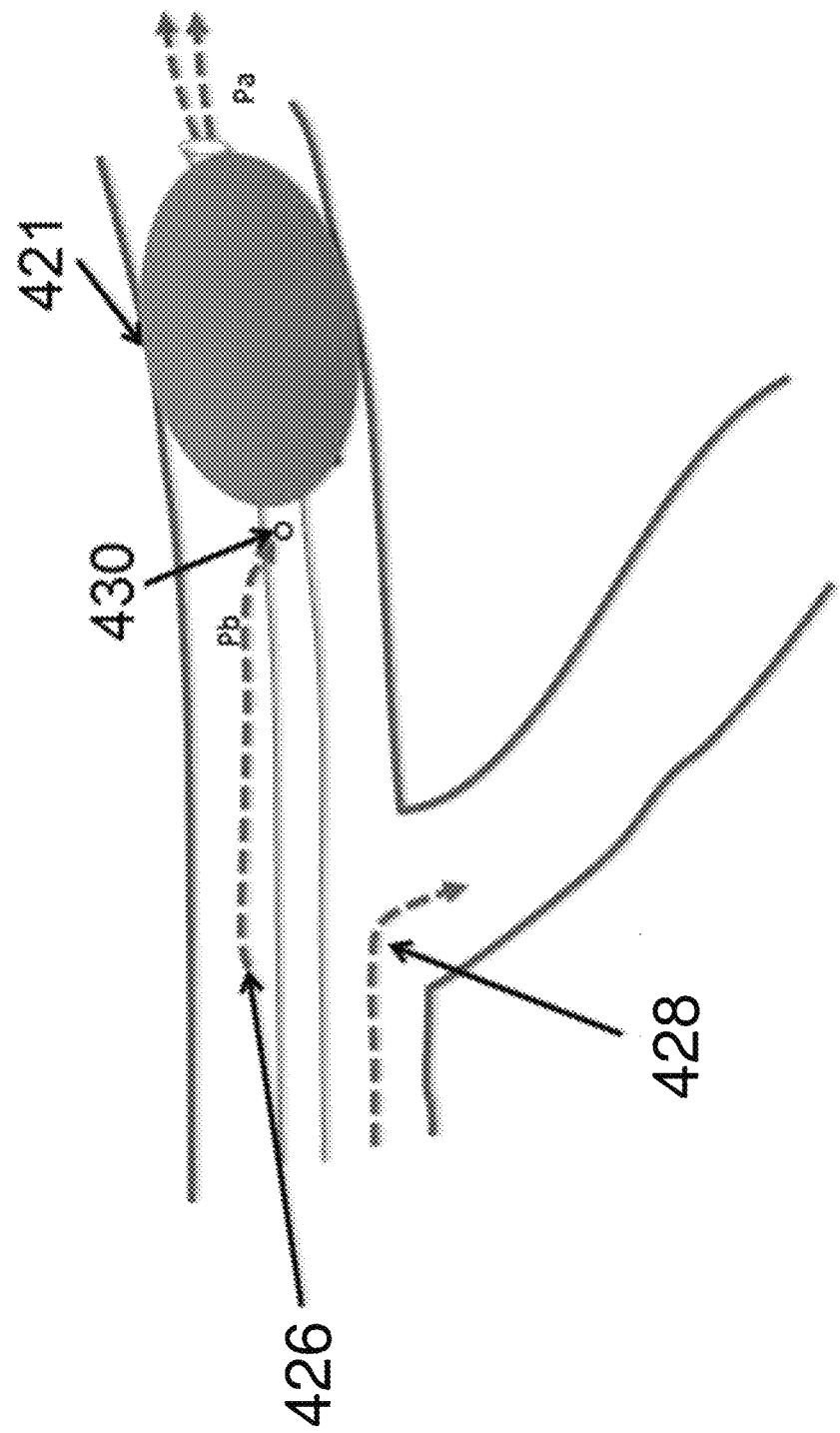

FIGS. 4A-4B show another example imposed minimum conductance system according to the principles herein.

Rather than an extra lumen under the imposed minimum conductance component (as shown in FIGS. 3A-3B), FIGS. 4A-4B show example imposed minimum conductance systems that include one or more holes or orifices 430 in the shaft of the device, just proximal to the component 421 (such as but not limited to a balloon). In these example systems, a fraction of the flow 424 that the device directs towards its distal tip leaks out through the one or more holes (or orifices) 430 prior to reaching the occlusion. FIG. 4A also shows the direction of blood flow 428. FIG. 4A illustrates an example when the value of pressure Pb is smaller than pressure Pa, which results in a backward flush flow (illustrated as flow 424). FIG. 4B shows the example imposed minimum conductance system for a scenario where Pb is large enough relative to than Pa such that a forward flush flow 426 results.

Figure 4C:
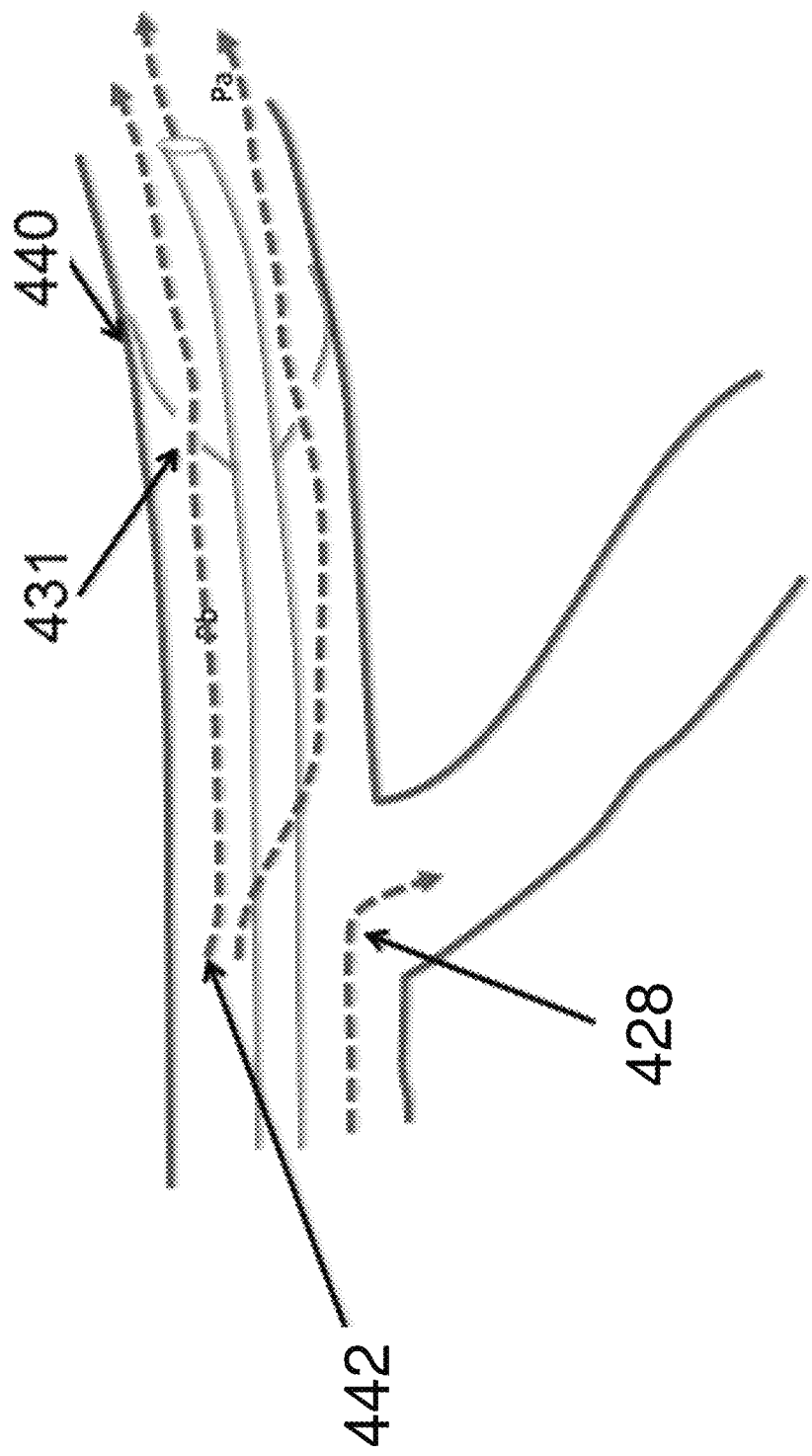
FIG. 4C shows an example of another catheter system, according to principles of the present disclosure.

FIG. 4C shows another example imposed minimum conductance system according to the principles herein. The example imposed minimum conductance system includes an imposed minimum conductance component (a spring driven membrane 440) including one or more holes (or apertures) 431. The one or more holes (or apertures) 431 are used to control fluid flow, and provide the minimum conductance. In the example imposed minimum conductance system of FIG. 4C, membrane 440 is illustrated in cross-section. However, membrane 440 includes one or more substantially solid membrane portions deployed symmetrically about the device shaft (similarly to the deployment of an umbrella). FIG. 4C also shows the direction of blood flow 428 and the fraction of the fluid flow 442 that leaks out through the one or more holes (or apertures) 431 of the imposed minimum conductance component.

Figure 4D:
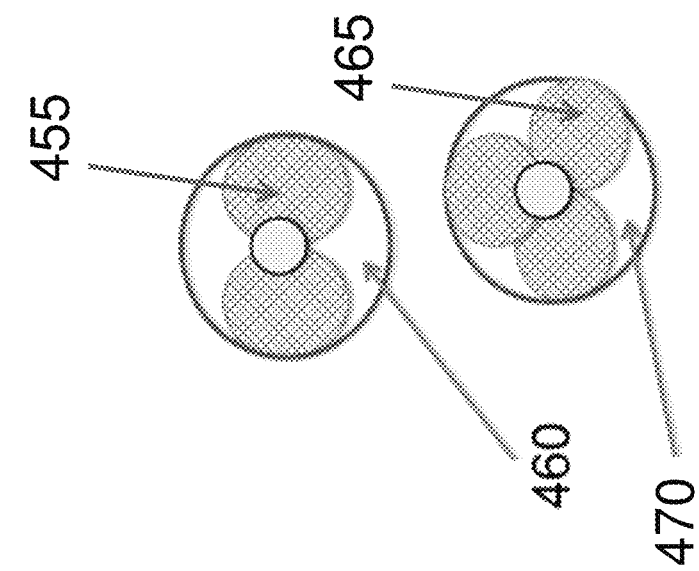
FIGS. 4D(i) and 4D(ii) an example of another catheter system, according to principles of the present disclosure.
Figure 4D:
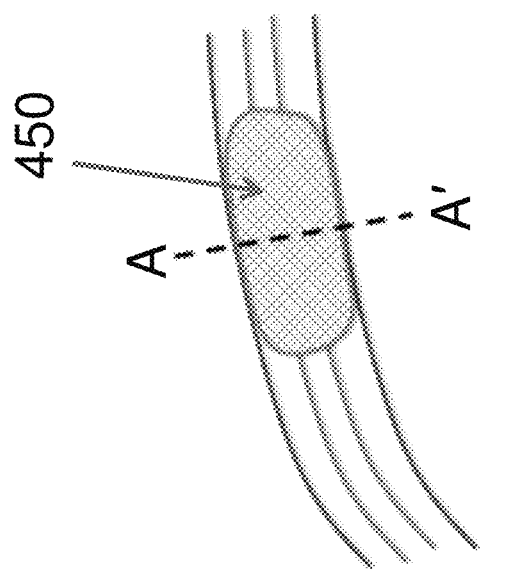

FIGS. 4D(i) and 4D(ii) show other example imposed minimum conductance systems according to the principles herein. The example system of FIG. 4D(i) includes a multi-lobed soft balloon (or other structured balloon) 450 that includes gaps in sealing the vasculature, between the lobes of the balloon, to provide the minimum conductance. In various examples, the multi-lobed soft balloon (or other structured balloon) 450 can be formed with two, three or more lobes. FIG. 4D(ii) shows cross-section views (through line A-A' shown in FIG. 4D(i)) of different examples of a multi-lobed soft balloon (or other structured balloon) 450. As non-limiting examples, the imposed minimum conductance system can include a two-lobed soft balloon (or other two-lobed structured balloon) 455 that includes gaps 460, or a three-lobed soft balloon (or other three-lobed structured balloon) 465 that includes gaps 470.

Figure 5A:
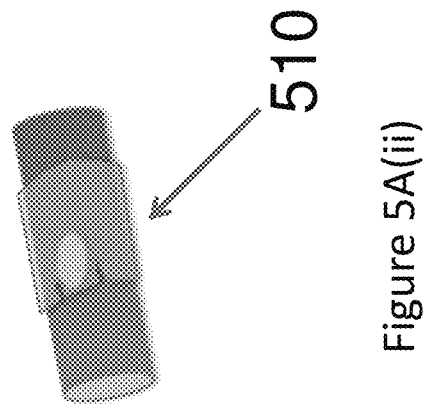
FIGS. 5A(i) and 5A(ii) show an example of a biased valve on an aperture in an example catheter system, according to principles of the present disclosure.
Figure 5A:
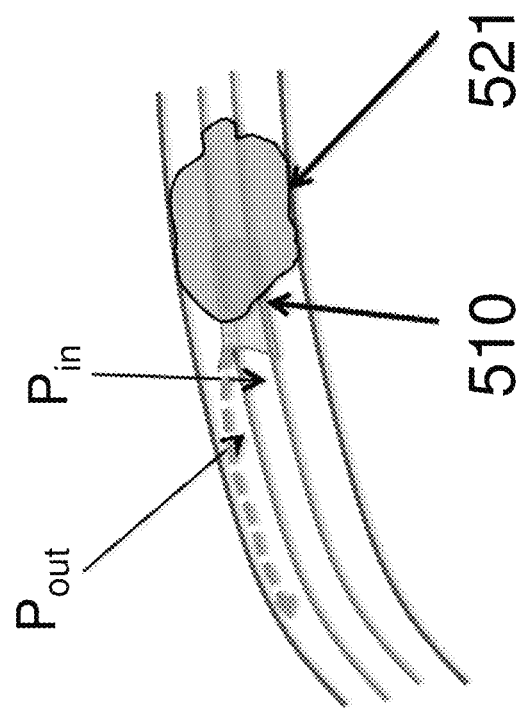

FIGS. 5A(i)-C show other example imposed minimum conductance systems according to the principles herein. In the example system of FIG. 5A, a biased valve 550 is used to add control of the direction of flushing flow to the minimum conductance. Therefore, the directionality might create a fixed-constant flow in the direction supported by the pressure difference across the means. As an example, the pressure difference in the vasculature can be such that the shift in blood pressure at the injection point branch due to each heart beat changes sign, i.e., changes from a positive pressure value to a negative value based on systolic/diastolic pressure variation. The example imposed minimum conductance system can be configured such that, based on the sign (i.e., direction) of the pressure differential, the flushing flow may be 'on' during only a portion of the heartbeat cycle, achieving a "fixed-average" minimum conductance rather than a "fixed-constant" minimum conductance.

FIG. 5A(i) shows an example imposed minimum conductance system that includes a biased valve 510 on an aperture in a catheter lumen that includes a component 521 (such as but not limited to a soft balloon). The parameters $P_{in}$ and $P_{out}$ are values of pressures inside the lumen and outside, proximal to the soft balloon 521. In this example, the distal region is the region where the flow rate and pressure are dominated by the flow passed through the lumen and injected through the distal tip. In general, if $P_{out}$ is driven by the heart, the value of $P_{out}$ has a similar cycle as the heart beats, reaching a local maximum and minimum in each cycle. FIG. 5A(ii) shows an example biased valve that can be implemented in the example system of FIG. 5A(i). FIG. 5A(ii) shows an example biased valve 510 mounted to portion of the shaft of a catheter, with a hole coupling the inside lumen of the shaft to the exterior and a flexible plastic flap, larger than the hole and anchored on at least one side, overlaying the hole. The example biased valve is configured such that a positive pressure difference (pressure inside shaft greater than pressure outside) can cause the flexible plastic flap to open, allowing fluid to flow outwards, and a negative pressure difference (pressure inside shaft lower than pressure outside) causes the flexible plastic flap to close and seal against the edges of the hole, blocking inward flow of fluid.

Figure 5B:
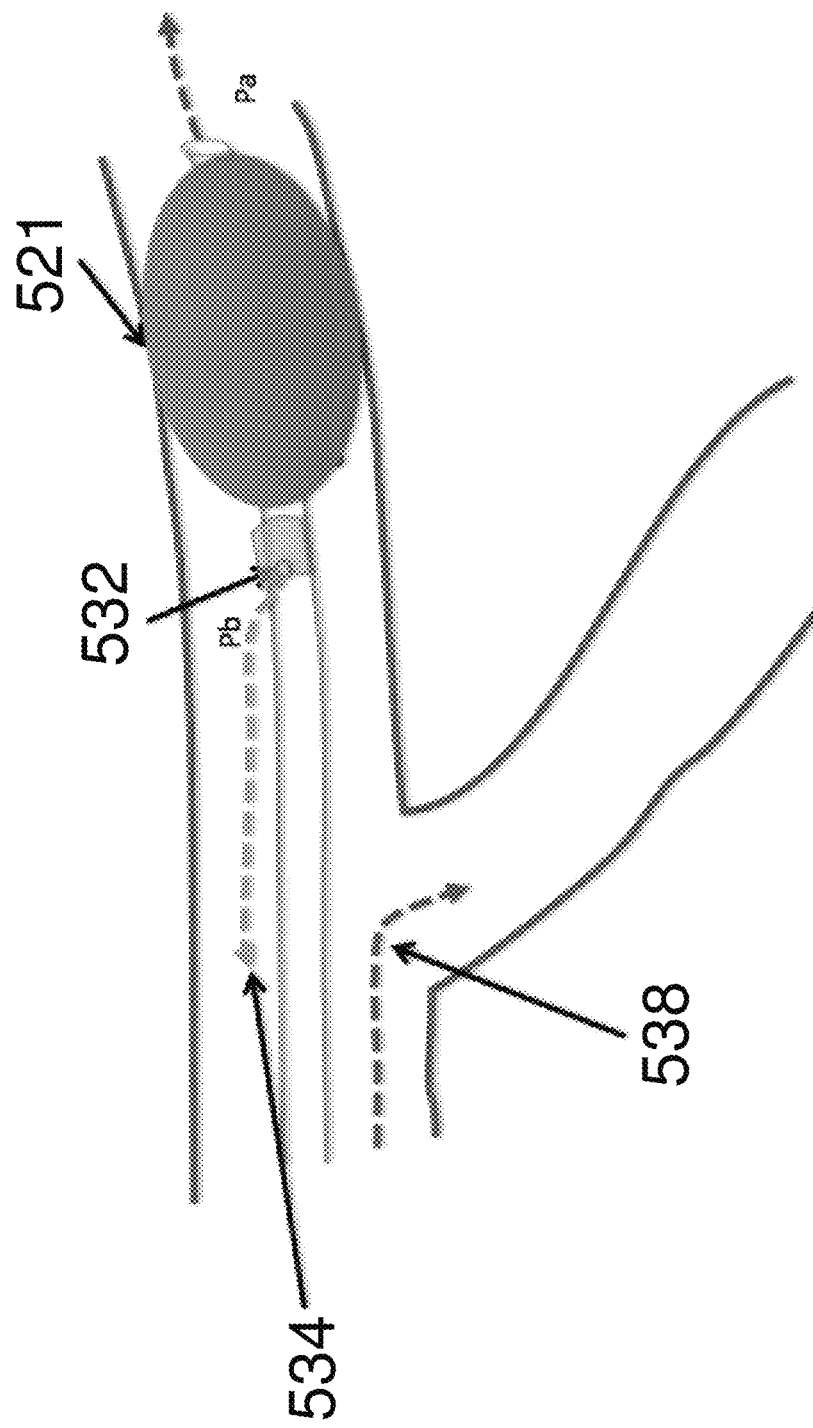
FIG. 5B shows an example of a biased valve on an aperture in an example catheter system, according to principles of the present disclosure.

FIG. 5B shows an example imposed minimum conductance system that includes a biased valve 532 coupled to a component 521. The biased valve 532 includes a flap that is configured to open and allow flow of fluid out of the central lumen of the injection member, but not allow flow into the lumen. That is, the biased valve 532 allows flow 534 when the value of pressure $P_b$ is lower than pressure $P_a$, which occurs during certain time intervals of the heartbeat cycle. FIG. 5B shows the fraction of the flow 534 through the flap of the biased valve 532 and the direction of blood flow 538. In this example, only a small fraction of blood injected into the body from the extracorporeal circuit is used to flush the dead zone (i.e., the flow 534 through the biased valve).

Figure 5C:
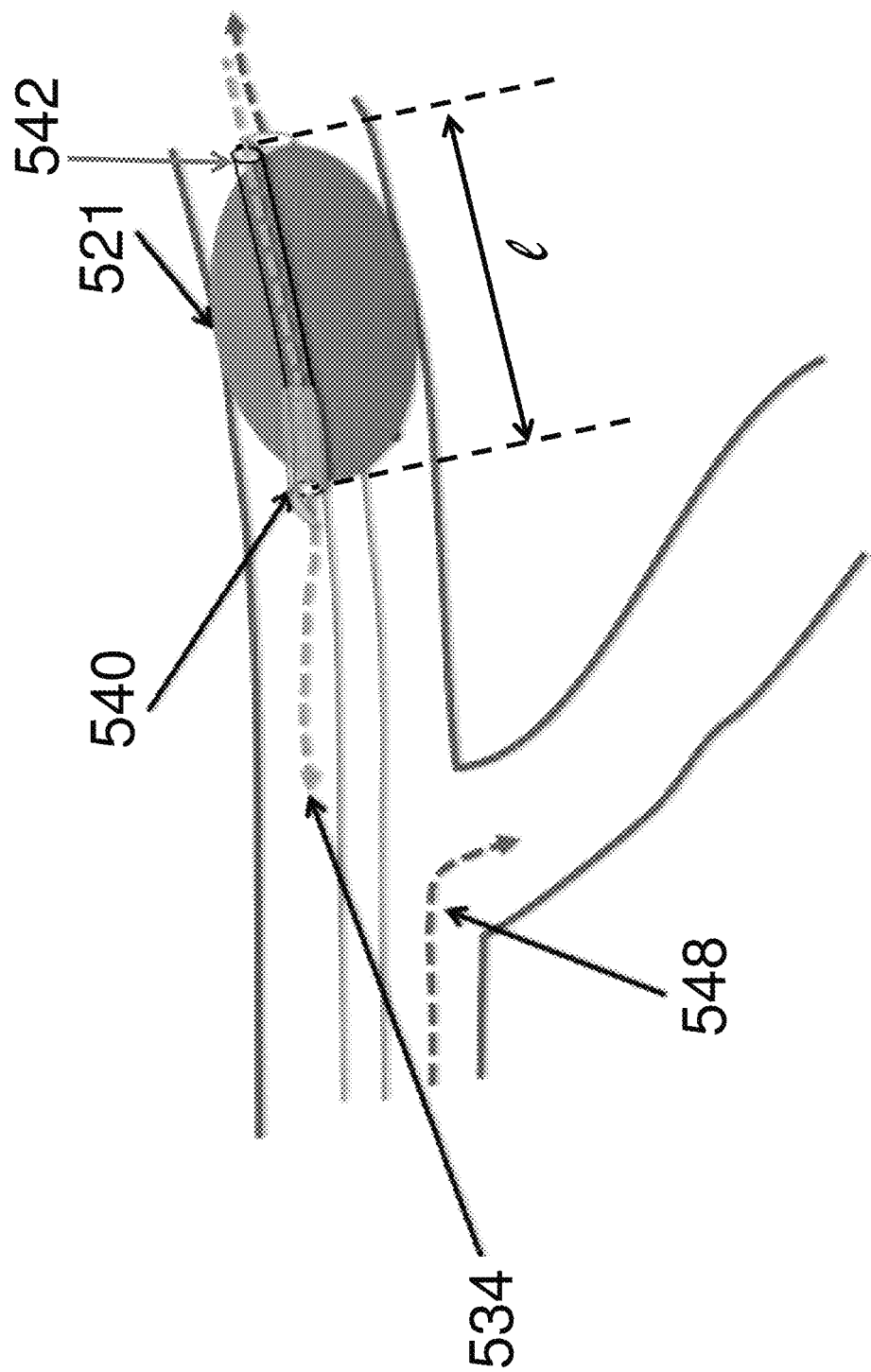
FIG. 5C shows an example of a biased valve on an aperture in an example catheter system, according to principles of the present disclosure.

FIG. 5C shows an example imposed minimum conductance system that includes a flap acting as a biased valve 540 on an end of a bypass lumen 542. The lumen 542 has a discrete length l, and is disposed along the shaft of the injector member and under the component 521, similar to the imposed minimum conductance systems shown in FIG. 3A or FIG. 3B. The coupled action of the biased valve 540 and the bypass lumen 542 provide a minimum conductance for flow to flush the dead zone (or low-flow zone). FIG. 5C shows the fraction of the flow 544 through the flap of the biased valve 540 and the direction of blood flow 548. The flap of the biased valve 540 could be mounted on either the proximal end or distal end of the bypass lumen 542, thereby allowing the direction of flushing flow to be selected by design. That is, if a flap configured to allow fluid conduction only outwards is mounted at the proximal end of lumen 542 (as shown in FIG. 5C), the distal injected blood flows back to flush. If the flap is mounted at the distal end of lumen 542, the normal blood flow from the branch flushes forward and mixes with the injected blood at the vascular injection point. The detailed operation is partly dictated by the applied pressure difference between the $P_b$ (pressure before the lumen 542) and $P_a$ (pressure after the lumen 542), as the biased valves can be configured to allow flow in only one direction. This example implementation would be beneficial if the values of pressure $P_a$ and $P_b$ are sufficiently close such that changes in $P_b$ from the systolic/diastolic pressure change with the heartbeat causes the biased valve to open during certain time intervals in each heart cycle.

According to the principles herein, an example imposed minimum conductance component, or an example system including a imposed minimum conductance component, can be used for providing selective thermal therapy. The example imposed minimum conductance component can be coupled to any system that is configured to apply a selective thermal therapy. In any example implementation, the imposed minimum conductance component according to the principles herein can be used in place of the usual occlusion element. The imposed minimum conductance component can be disposed proximate to the distal tip of at least one injector member an injector member of the system for applying the selective thermal therapy. As non-limiting examples, an imposed minimum conductance component according to the principles herein can be coupled to any system for applying selective thermal therapy in the art, such as the system disclosed in U.S. Pat. No. 7,789,846 B2, or international (PCT) Application No. PCT/US2015/033529.

In any example herein, the imposed minimum conductance component can be formed with an atraumatic surface, a hydrophilic coating, or a drug coating, or any combination thereof.

Figure 6A:
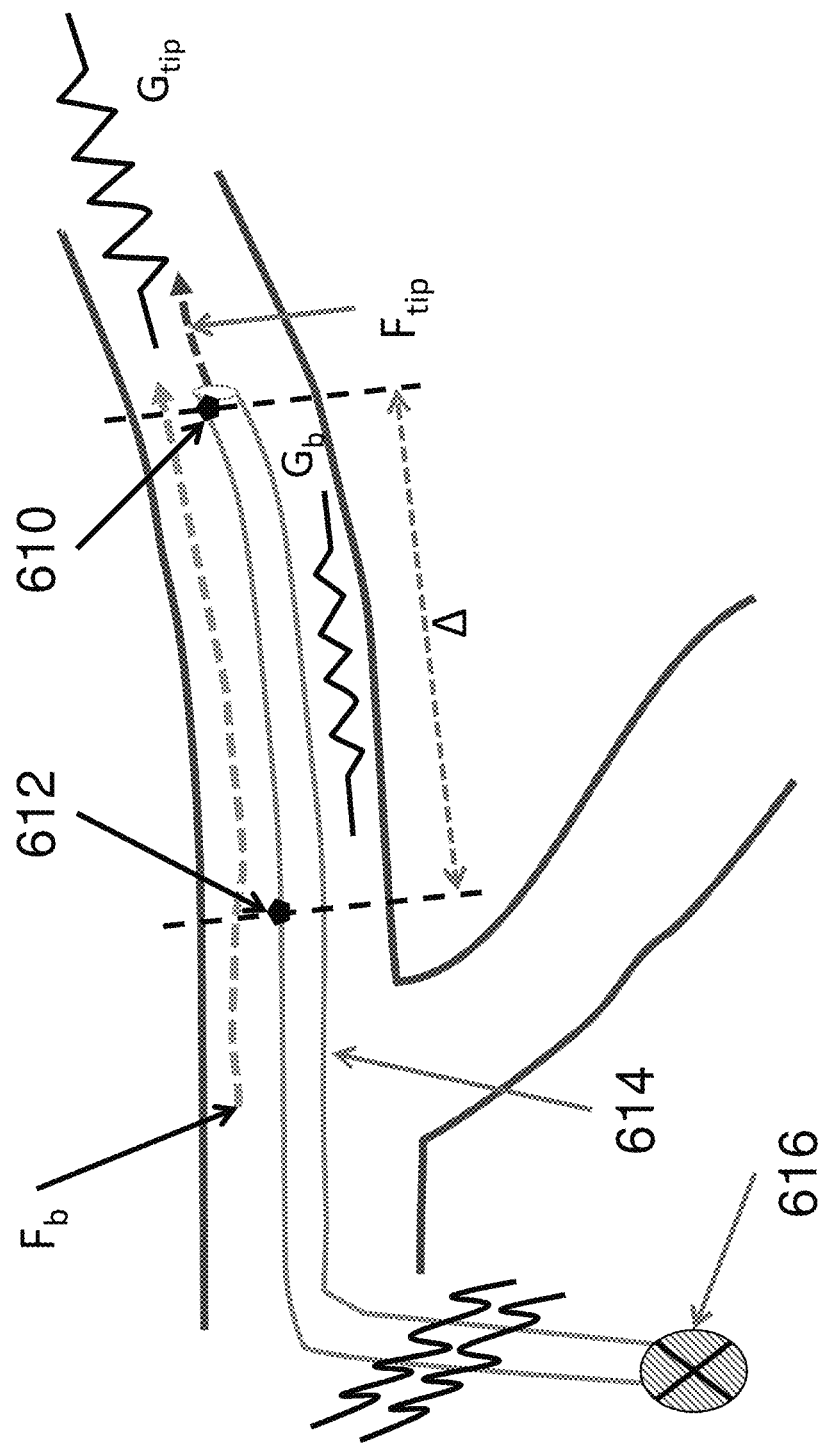
FIG. 6A shows an example injector member coupled to pressure sensors in an example catheter system, according to principles of the present disclosure.

FIG. 6A shows an example controlled flow partitioning system of the present disclosure. The example controlled flow partitioning system includes a first pressure sensor 610 and a second pressure sensor 612. The first pressure sensor 610 can be disposed proximate to the tip of the injector member 614 of a catheter, and the second pressure sensor 612 can be disposed on the injector member 614 at a pre-defined separation (Δ) proximal to an operator as measured from the tip (or from pressure sensor 610). As non-limiting examples, the pre-defined separation (Δ) can be about 2 cm, about 5 cm, about 8 cm, about 12 cm, about 15 cm, about 20 cm, about 25 cm, or about 30 cm. In various non-limiting examples, one or both of pressure sensors 610 and 612 can be implemented as silicon-based sensors embedded in the catheter wall (with electronic (wired) readout), or optical fiber-based pressure sensors that use fibers in lumens in the catheter wall to provide readout to appropriate computing interface systems at the proximal end of the catheter. In another example implementation, one or both of pressure sensors 610 and 612 is configured to use a simple wall lumen, having distal opening at the location as illustrated in FIG. 6A, filled with an incompressible fluid, and an external pressure sensor mounted on a fluid connector at the proximal end of the catheter to measure the static or low frequency pressure conducted by the fluid column of the lumen. Pressure sensor 610 can be configured to measure the pressure proximate to the tip ($P_{tip}$) and pressure sensor 612 can be configured to measure the pressure ($P_b$) proximate to the injector member 614. FIG. 6A also shows examples of the direction of blood flow at flow rate $F_b$ around the catheter and the injected blood flow at flow rate $F_{tip}$ at the tip of the injector member.

As also shown in FIG. 6A, the catheter can be coupled to a flow rate source 616 of an extracorporeal system. In an example implementation, the fluid can be volume flow driven rather than being pressure driven. When fluid is injected into the vasculature through the tip ($F_{tip}$), it mixes with fluid from upstream ($F_b$) and flows through the downstream conductance $G_{tip}$. The upstream flow passes through the conductance $G_b$, shown in FIG. 6A as occurring in the space between the wall of the artery (or vein) and the catheter. It can be difficult to measure or predict directly a value for conductance $G_b$. Even with the pressure sensors 610 and 612 being disposed to measure $P_b$ and $P_{tip}$, it can be difficult to measure $F_b$ directly if $G_b$ is unknown. Example systems and methodologies according to the principles herein can be used for determining a value for $G_b$.

In an example, the flow rate source can be used to control a volumetric flow rate. The example flow rate source can be, but is not limited to, a displacement pump, a syringe pump, or a rotary pump.

In an example, the flow rate source can be used to control the flow rate such that fluid injected at the distal tip flows as a series of volume impulses. In this example, the series of volume impulses can be modeled according to a step function. The flow rate source can be a pump that executes instructions from a processing unit of a console to deliver each of the impulses of the series of impulses, or a pump that is initiated based on a first signal from the console and continually delivers the step function impulses until a second signal from the console causes the pump to cease operation.

In other examples, the flow rate source can be used to control the flow rate such that fluid flows according to other types of functional forms, such as but not limited to a sinusoidal, sawtooth, or otherwise cyclical functional form.

In any example herein, the flow rate source can be used to control the flow rate to establish the flow rate pattern. As described above, the flow rate pattern can be based on an arbitrary waveform or other types of functional forms, such as but not limited to a sinusoidal, sawtooth, or otherwise cyclical functional form.

In a non-limiting example according to the principles of FIG. 6A, an injector member is coupled to two pressure sensors, with the injector member being driven by an external flow rate controlling means to allow measurement or computation of values for the proximal exterior conductance and the distal exterior conductance. The example system enables deduction of flow around the injector member of the catheter from data indicative of pressure measurements.

A controlled flow partitioning system is provided for determining the two conductances, including the system illustrated in FIG. 6A. The first conductance, referred to as the proximal conductance ($G_b$), is the conductance in the vascular space outside the catheter between the planes defined by the two pressure sensors 610 and 612. The second conductance, referred to as the distal conductance ($G_{tip}$) is the conductance from the tip to blood return to the core system (or ground in a flow sense). Both of these conductances generally are not deducible without measurement, since the computation would use data indicative of the size and shape of the local vasculature. In the case of $G_{tip}$, computation would use data indicative of the state of and/or the amount of damage of the vasculature bed. Knowledge of values of both of these conductances may offer clinical benefit, since they represent a measurement of the local state of vasodilation/vasoconstriction of the patient. Using the pressure sensors 610 and 612 to measure $P_b$ and $P_{tip}$, if the conductance between them is a controlled one as in the prior described imposed minimum conductance, then the flow can be estimated using flow $F_b = G_b(P_b - P_{tip})$. In an example implementation where the computation of $G_b$ includes data indicative of the surface of the vein or artery, it may not be possible to determine $G_b$ beforehand. In general, $G_{tip}$ cannot be determined prior to an operation or other medical procedure that involves placement of the injection member.

Example systems and methodologies are provided herein for computing both $G_b$ and $G_{tip}$ in situ for a patient during an operation or other medical procedure. Using a linear approximation, balancing the flow around the distal tip of the injection member can be expressed using two equations as follows:

$$F_b = G_b(P_b - P_{tip}) \quad (1)$$

$$(F_b + F_{tip}) = G_{tip}(P_{tip}) \quad (2)$$

The value for $F_{tip}$ can be set from the pump (such as but not limited to flow rate source 616). The example system of FIG. 6A can be used to measure values for pressure $P_b$ and pressure $P_{tip}$. Using these values, the equations can be reduced to:

$$G_{tip} = F_{tip}/P_{tip} + Gb(P_b - P_{tip})/P_{tip} \quad (3)$$

where Gtip and Gb are the unknowns. During an operation or other medical procedure that uses the injection member to return blood to the body, the initial injected flow at time $T_0$ can be used as $F'_{tip}$ (as a non-limiting example, about 250 ml/min). At time $T_1$ that value of flow might be changed to $F''_{tip}$ (as a non-limiting example, about 275 ml/min, a 10% increase). These non-limiting example values of flow at times $T_0$ and $T_1$ can be chosen to fall within a desirable clinical range for the specific anatomy at the injection point and the specific clinical application. The example system of FIG. 6A can be used to measure values for pressure $P_b$ and pressure $P_{tip}$ at the time points $T_0$ ($P'_b$ and $P'_{tip}$) and $T_1$ ($P''_b$ and $P''_{tip}$). Using the four different values of pressure and two different values injection flows in equation (3), i.e., introducing $F'_{tip}$, $P'_{tip}$, $P'_b$ at time $T_0$ and $F''_{tip}$, $P''_{tip}$, and $P''_b$ at time $T_1$, generates two (2) equations, each with two (2) unknowns. These equations can be used to compute values for $G_b$ and $G_{tip}$. It is readily apparent to one of ordinary skill in the art that equations (1), (2) and (3) are non-limiting examples of equations relating flow, conductance, and pressure in a vascular region. Other equations, including more complex versions of the equations, can be applicable. For example, equations in which conductance is not independent of pressure, but itself is a function of pressure, may also be addressed by using repeated measurements of the pressures at different values of applied flow $F_{tip}$, to establish more equations and allow solving for forms of conductance (G) that are linear, or even quadratic, or higher order functions of pressure.

As described herein, the flow rate source can be used to control the flow rate such that fluid injected at the distal tip flows according to a step function, or other types of functional forms, such as but not limited to a sinusoidal, sawtooth, or otherwise cyclical functional form. In other examples, the flow rate can be modeled based on measurements of a response function with fluid flow, and solving for an applicable functional form.

Example systems and methodologies are provided herein for computing both $G_b$ and $G_{tip}$ in situ for a patient during a lengthy operation or other medical procedure. As a non-limiting example, such a lengthy operation (or other medical procedure) could last on the order of hours to days. An example methodology can include applying a step change to $F_{tip}$ (i.e., a discrete change in value from a baseline) for a short interval of time ($t_1$) at regular repeated cycles during the operation or other medical procedure. As a non-limiting time the step change can be applied to $F_{tip}$ for the first 5 minutes (i.e., $t_1 = 5$ minutes) of each hour of the operation or other medical procedure. At the end of time interval $t_1$, the value of $F_{tip}$ is returned to the baseline value. This example methodology for modifying the value of $F_{tip}$ can be used for measuring $G_b$ and $G_{tip}$ at each hour during the lengthy operation or other medical procedure, using the methodologies described herein. These example systems and methodologies have clinical application in monitoring the vascular state (vasodilation/vasoconstriction) or detecting the process of thrombus formation or time of thrombolysis.

Another example clinical application of the example systems and methodologies is as follows. During an operation or other medical procedure, with values computed for $G_b$ and $G_{tip}$, the quantity of flow $F_b$ that is flushing the space proximal to the tip can be determined from the measured pressure $P_b$ and $P_{tip}$. If flow $F_b$ falls out of a desired range of values, $F_{tip}$ may be adjusted to adjust $F_b$.

Another clinical application of the systems and methodologies is determination of the heat capacity of the blood applied to the tissue. During the operation or other medical procedure, $F_b$ and $F_{tip}$ can mix in the zone distal to the tip. If the blood flow $F_b$ is at a first temperature and the blood flow injected $F_{tip}$ is at a second temperature different than the first temperature, then the heat capacity of the blood applied to the tissue in the distal zone may be calculated directly and adjustment of the temperature of the injected blood may be used to compensate for warm or core blood flow $F_b$. Alternatively, the process of controlled rewarming may be done by adjusting the ratio of flows $F_b:F_{tip}$, as well as their temperature difference. An example methodology for measuring $G_b$ and $G_{tip}$ described herein can be applied a single time or multiple times during an operation or other medical procedure. The method can be generalized to use more than one step change in $F_{tip}$ in which case the operator can measure values for $G_b$ and $G_{tip}$ to determine how they might vary out of the linear approximation of equations (1-3). An operator can implement an example methodology according to the principles herein by, e.g., directly setting $F_{tip}$, recording the sensor recordings, and using a computing device to perform the computations. In another example implementation, a computing device or system herein can include at least one processing unit that is programmed to execute processor-executable instructions, to cause a controller of an example system to implement the measurement routine automatically as described herein for measuring values for $G_b$ and $G_{tip}$. The example system can be configured to allow a user to set a nominal value of $F_{tip}$ and execute processor-executable instructions for performing an automatic measurement of $G_b$ and $G_{tip}$ at the desired time intervals, such as but not limited to, every 30, or 45, or 60 minutes or other time interval. In any example herein, the computing device can be a console.

Figure 6B:
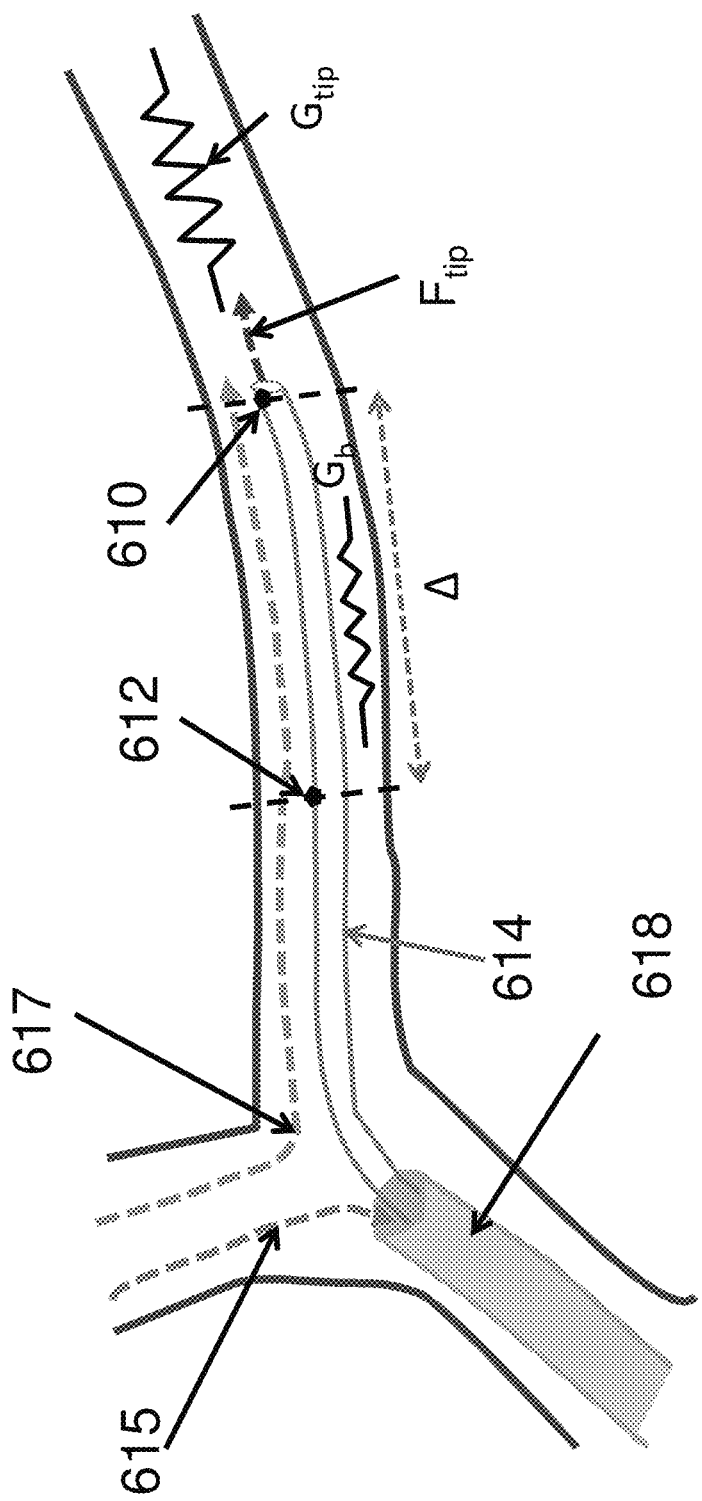
FIG. 6B shows another example injector member coupled to pressure sensors in an example catheter system, according to principles of the present disclosure.

FIG. 6B shows an example controlled flow partitioning system according to the principles herein. The example system includes two pressure sensors in use with a concentric cylinder two-port catheter to support an independent local extracorporeal loop. As shown in FIG. 6B, two pressure sensors 610' and 612' are coupled to an insertion member 614 that is part of an extracorporeal circuit access catheter of concentric shaft type. In the example, the outer shaft 618 supplies blood to the extracorporeal circuit 618 and the inner shaft 614 acts as an injection member to return blood to a location in the body. FIG. 6B also shows dashed line 615 for blood flow out to the extracorporeal circuit and dashed line 617 for blood flow around a catheter (Fb). As non-limiting examples, U.S. Pat. Nos. 7,704,220 and 7,789,846, disclose examples of concentric extracorporeal access catheters that can be implemented in one or more example systems according to the principles herein.

FIGS. 6C and 6D show example systems that can be used to compute values of conductance in a region of the vasculature proximate to the heart, according to principles herein. In the examples of FIGS. 6C and 6D, the example system is shown disposed in a region of the aortic arch. As shown in FIG. 6C, the example system includes pressure sensors 610 and 612 coupled to a catheter member 620. In this example, the pressure sensor measurements can be used to compute the conductance as described herein. In an example, using the pressure measurements, the conductance can be computed according to the example method described hereinabove for computing both $G_b$ and $G_{tip}$ in situ. In the example of FIG. 6C, fluid flow can be introduced from a distal tip of the catheter member 620. FIG. 6D shows another example system that is similar to FIG. 6C, with the exception that the catheter 620 includes a proximal port 622 that allows fluid flow from a more intermediate region of the catheter member 622.

In any example system, method, device, and apparatus herein, the fluid injected through the injector member of may be mixed with the fluid passing through the exterior space around the catheter or device (exterior fluid). If the fluid flows mix, they form a mixed fluid in the region distal to the point of injection (also referred to herein as a mixed distal flow). If a drug or pharmacological agent of a known concentration (in mg/ml or other units of mass/volume) is added to the injected fluid, the concentration of drug or pharmacological agent in the distal mixed fluid is unknown, unless the ratio of the exterior fluid and injected fluid flow rates is known. The example systems described herein can be used to set the exterior conductance (imposed minimum conductance component) or quantify the exterior conductance (controlled partitioning flow system). Based on the conductance data, the exterior fluid flow rate can be measured or computed. With the computed value of exterior fluid flow rate, and the injected flow rate set by the pump system (or other system) coupled to the injector member, the concentration of drug or pharmacological agent added to the injected fluid can be adjusted to achieve the desired concentration of drug in the distal fluid mixture.

In any example herein, the drug or pharmacological agent can be any substance used to diagnose, cure, treat, or prevent a disease. For example, the drug or pharmacological agent can include an electrolyte solution, nanoparticles, biological agent, small molecule, large molecule, polymeric material, biopharmaceutical, or any other drug or pharmacological agent that can be administered in the blood stream.

An example system according to the principles herein can be used for providing at least two zones of selective thermal therapy. The example system includes an extracorporeal circuit. The example extracorporeal circuit includes an injector member including a distal tip disposed at a vascular location, an imposed minimum conductance component disposed proximate to the distal tip. The example system can also include a first port to withdraw blood from the body, a second port to return blood to the body, a first pump disposed between the first port and the second port to pump blood from the first port to the second port, a branching section positioned between the first pump and second port, a third port coupled to the branching section, the third port being positioned on an extracorporeal side of the injector member, and a second pump positioned between the branching section and the third port. The second pump can be configured to control a flow rate out the branching section into the injector member through the third port. The example system can also include a first heat exchanger disposed between the first port and the second port, and a second heat exchanger disposed between the second pump and the injector member. The first heat exchanger can be configured to set a temperature of blood injected into the second port to a first temperature level. The second heat exchanger can be configured to set the temperature of blood injected into the injector member to a second temperature level different from the first temperature level. The first heat exchanger can be disposed between the branching section and the first port or between the branching section and the second port.

The example system for providing at least two zones of selective thermal therapy can include an occlusion component, or an imposed minimum conductance component, disposed proximate to the distal tip of the injector member.

Another example system for providing at least two zones of selective thermal therapy according to the principles herein can include an extracorporeal circuit including an injector member comprising a distal tip disposed at a vascular location. The example system can further include a controlled flow partitioning system proximal to the distal tip. The controlled flow partitioning system can include a first sensor for measuring flow proximate to a distal tip of the at least one injector member and a second pressure sensor for measuring a second pressure, the second pressure sensor being disposed proximal from the distal tip, at a distance greater than or approximately equal to twice a diameter of the vasculature. In other examples, the separation distance can be greater than or approximately equal to three, five, or ten times the diameter of the vasculature. In another example, the separation distance can be greater than about 1.0 cm proximal from the distal tip. The example system can also include a first port to withdraw blood from the body, a second port to return blood to the body, a first pump disposed between the first port and the second port to pump blood from the first port to the second port, a branching section positioned between the first pump and second port, a third port coupled to the branching section, the third port being positioned on an extracorporeal side of the injector member, and a second pump positioned between the branching section and the third port. The second pump can be configured to control a flow rate out the branching section into the injector member through the third port. The example system can also include a first heat exchanger disposed between the first port and the second port, and a second heat exchanger disposed between the second pump and the injector member. The first heat exchanger can be configured to set a temperature of blood injected into the second port to a first temperature level. The second heat exchanger can be configured to set the temperature of blood injected into the injector member to a second temperature level different from the first temperature level. The first heat exchanger can be disposed between the branching section and the first port or between the branching section and the second port.

The example system for providing at least two zones of selective thermal therapy can include an occlusion component, or an imposed minimum conductance component, disposed proximate to the distal tip of the injector member.

Figure 7A:
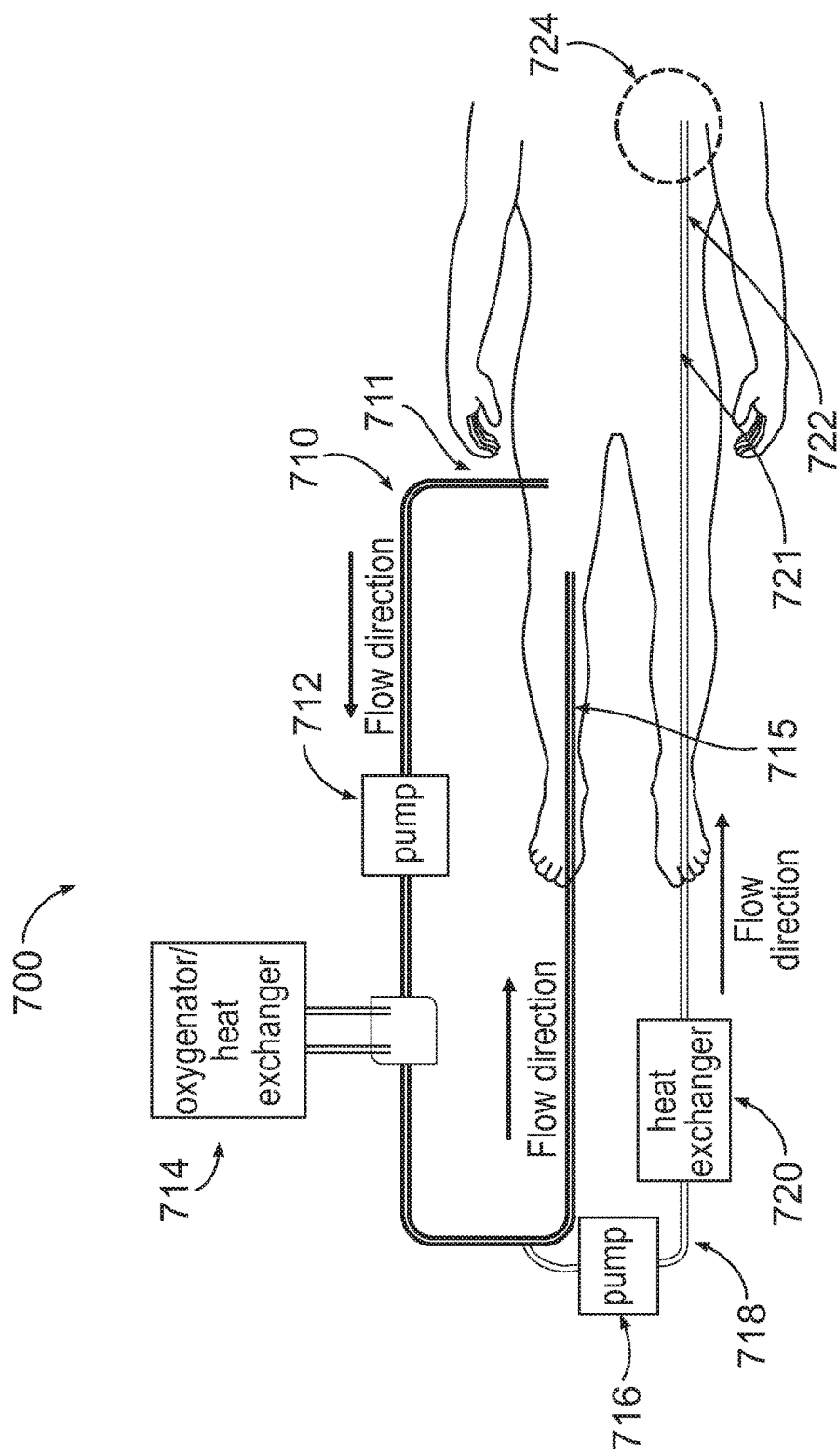
FIG. 7A shows an example extracorporeal circuit system, according to principles of the present disclosure.

FIG. 7A shows a schematic of an example three-port extracorporeal circuit for providing at least two zones of selective thermal therapy according to the principles herein. As a non-limiting example, the extracorporeal circuit can be implemented for controlling blood flow to the core and an attached local branch, with independent flow rate and temperature control. In the non-limiting example of FIG. 7A, the extracorporeal system 700 is a three port, two-zone, extracorporeal circuit in which a main veno-arterial (VA) extracorporeal loop 710 takes blood from the body via a first port 711 and returns it using a pump 712 and oxygenator/heat exchanger 714 via a second port 715. The example system can include a displacement or volume driven pump 716 located on a branch 718 of the main loop and pulls a controlled volume flow rate of blood out of the main circuit and injects it through an independent heat exchanger 720, a third port 721, and the distal injector member 722 to a local region 724 of a body. In a non-limiting example, branch 718 can be a local perfusion hypothermia branch. The non-limiting example system of FIG. 7A allows establishment of two independently controlled temperature zones in the body when deployed with appropriate zone temperature sensors. In other examples, the branch 718 can be coupled to main loop either before or after the main loop oxygenator 714, depending on the users desire for the injector member blood to be oxygenated or not. In these examples, if the system is used to apply localized hypothermia through the distal injector member, such as disclosed in International (PCT) Application No. PCT/US2015/033529, the absence of a concentric cylinder outflow on the injector member may cause an increase in the conductive cooling of that member catheter to the artery it is placed within. This effect may require some additional warming on the main circuit loop to achieve equivalent thermal targets in the body zones that are desired to be controlled.

Figure 7B:
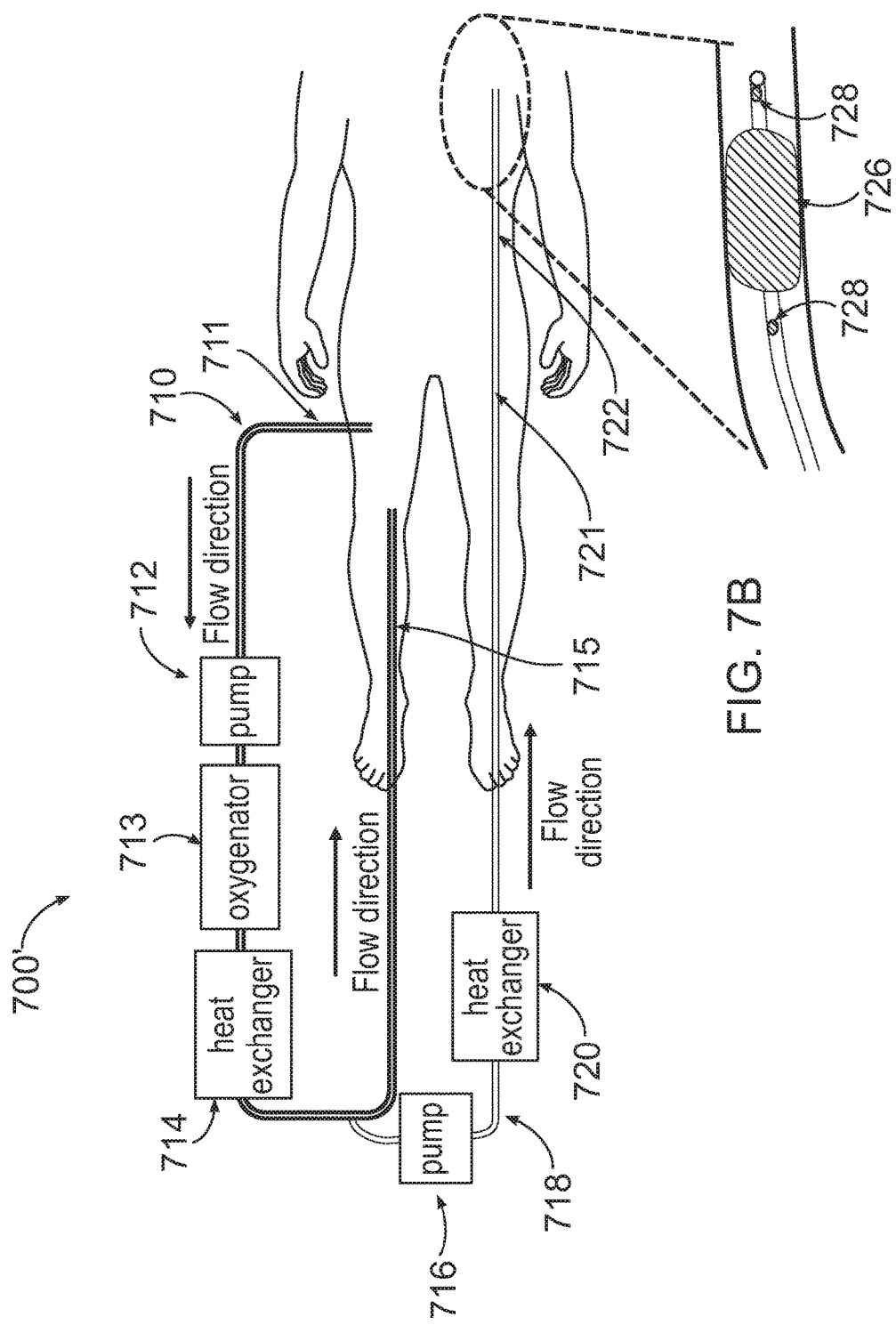
FIG. 7B shows another extracorporeal circuit system, according to principles of the present disclosure.

FIG. 7B shows another example extracorporeal circuit for providing at least two zones of selective thermal therapy according to the principles herein. Similarly to FIG. 7A, the extracorporeal system 700' of FIG. 7B includes a main VA extracorporeal loop 710 that takes blood from the body via a first port 711 and returns it using a pump 712, an oxygenator 713 and a heat exchanger 714 via a second port 715. In a non-limiting example, the oxygenator 713 and heat exchanger 714 can be a combined unit. The example system 700' also include a displacement or volume driven pump 716 located on a branch 718, to pull a controlled volume flow rate of blood out of the main circuit and inject it through an independent heat exchanger 720, a third port 721, and a distal injector member 722 to a local region of a body. In the example the extracorporeal system 700', the injector member can also include an occlusion means, an imposed minimum conductance component (according to any of the examples herein, including any of FIGS. 3A to 5C), or a pressure sensor pair coupled to the injector member (according to any of the examples herein, including FIG. 6A or 6B), or both a pressure sensor pair and either an occlusion means or an imposed minimum conductance component. In the non-limiting example system of FIG. 7B, the injector member 722 includes both a imposed minimum conductance component 726 and a coupled pressure sensor pair 728. In the example of FIG. 7B, the oxygenator 714 on the main loop is positioned before the local injector branch 718 and so the local injected blood is oxygenated.

Figure 7C:
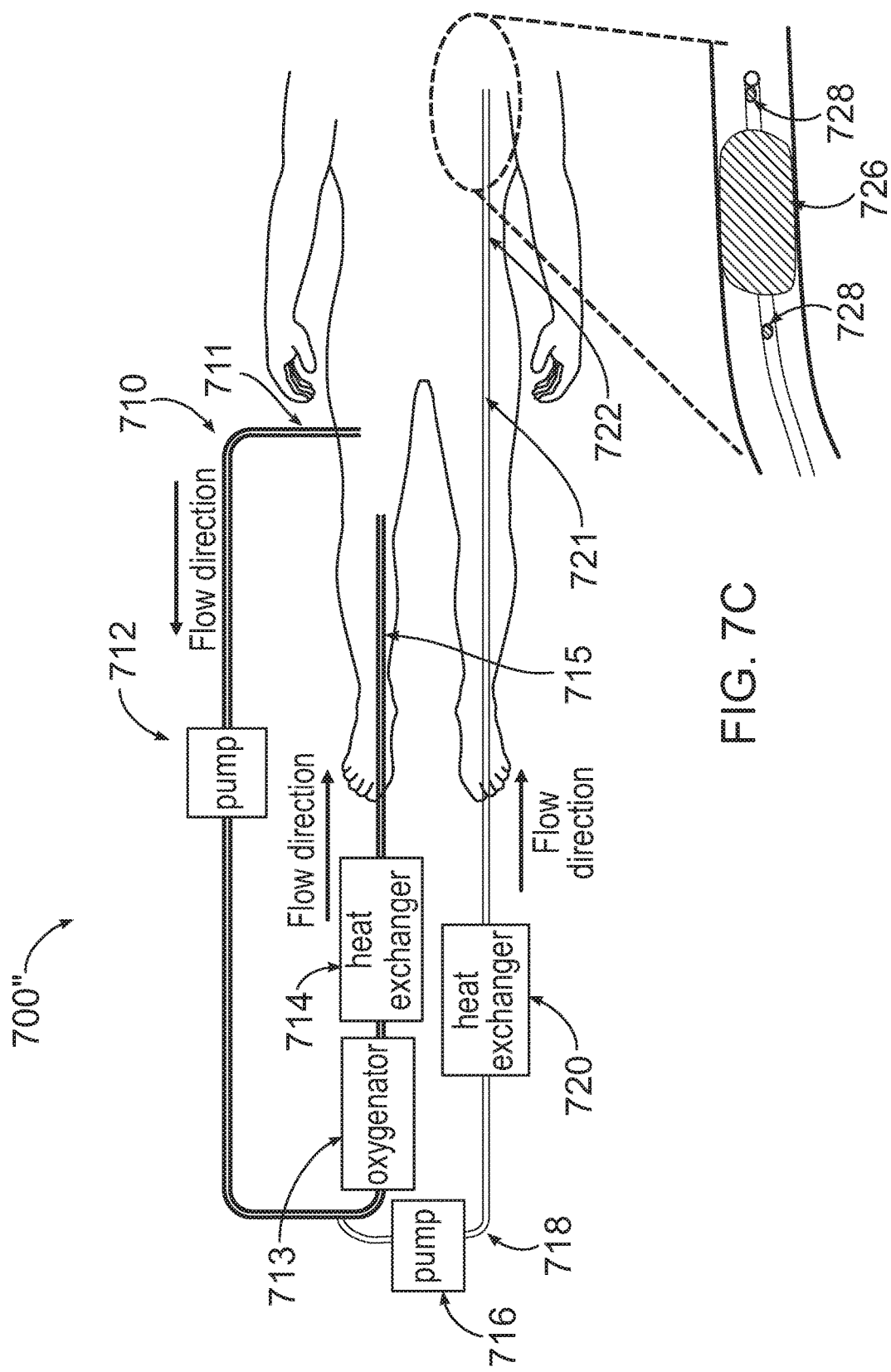
FIG. 7C shows another extracorporeal circuit system, according to principles of the present disclosure.

FIG. 7C another example extracorporeal circuit for providing at least two zones of selective thermal therapy according to the principles herein, which includes similar components to those described in connection with FIG. 7B. However, in the extracorporeal system 700" of FIG. 7C, the oxygenator 713 on the main loop is positioned along the loop after the local injector branch, and so the local injected blood is not directly oxygenated. In a non-limiting example, the oxygenator 713 and heat exchanger 714 can be a combined unit.

The non-limiting example system of any of FIG. 7A-7C can include temperature sensors coupled to regions of the body to allow provide measurement of temperature at the two independently controlled temperature zones in the body. For example, at least one temperature sensor can be disposed at or otherwise coupled to the region perfused by the second port and at least one temperature sensor can be disposed at or otherwise coupled to the local region of the body perfused by the distal injector member. The at least one temperature sensor disposed at or otherwise coupled to the region perfused by the second port can be configured to measure an average core body temperature and/or average system temperature of a portion of body. The at least one temperature sensor disposed at or otherwise coupled to the local region of the body perfused by the distal injector member configured to measure the temperature of the local region.

The non-limiting example system of any of FIG. 7A-7C can include temperature sensors coupled to at least one of the heat exchangers.

Other non-limiting example systems according to the principles of FIGS. 7A-7C can be configured for performing other procedures on the blood in the extracorporeal loops, such as but not limited to dialysis, oxygenation, purification, pharmacological manipulation, photolysis, or other procedures that can be useful on blood. Any one or more of these procedures could be performed on either the main loop or the branch or both (with differing amounts or quantities of one or more of the procedures being performed on the loop or the branch).

In the non-limiting examples of FIGS. 7A-7C, the maim loop is described as a VA loop. However, in other example implementations, the main loop can be a veno-venous (VV) loop instead of a VA loop. In an example VV loop, the blood is taken from the venous side of the vasculature, typically from the iliac or inferior vena cava, and returned into the vena cava, typically higher or closer to the heart. In another example, the VV may be implemented with a single puncture in the femoral vein, and a single dual lumen catheter can be used to place both the VV loop blood output and return, each using a lumen of the catheter.

An example system according to the principles herein can include one or more control consoles. The example consoles can include one or more user interfaces, configured to receive input representative of desired settings for one or more of the pumps, heat exchanges, and/or oxygenators of the example extracorporeal system main loop and/or local branch. The example console can include one or more processing units to execute processor-executable instructions to cause one or more of the pumps, heat exchanges, and/or oxygenators to change to a different setting of operation, and/or to maintain a particular setting of operation, over a period of time. In any example, the input can be received at the one or more user interfaces directly from a user or from another computing device. The example console can include at least one memory to store processor-executable instructions that can be implemented using the one or more processing units. The example console can be configured to store and/or transmit data indicative of the settings of the system and/or any measurement data derived based on execution of one or more procedures using the example system coupled to the console.

Figure 8A:
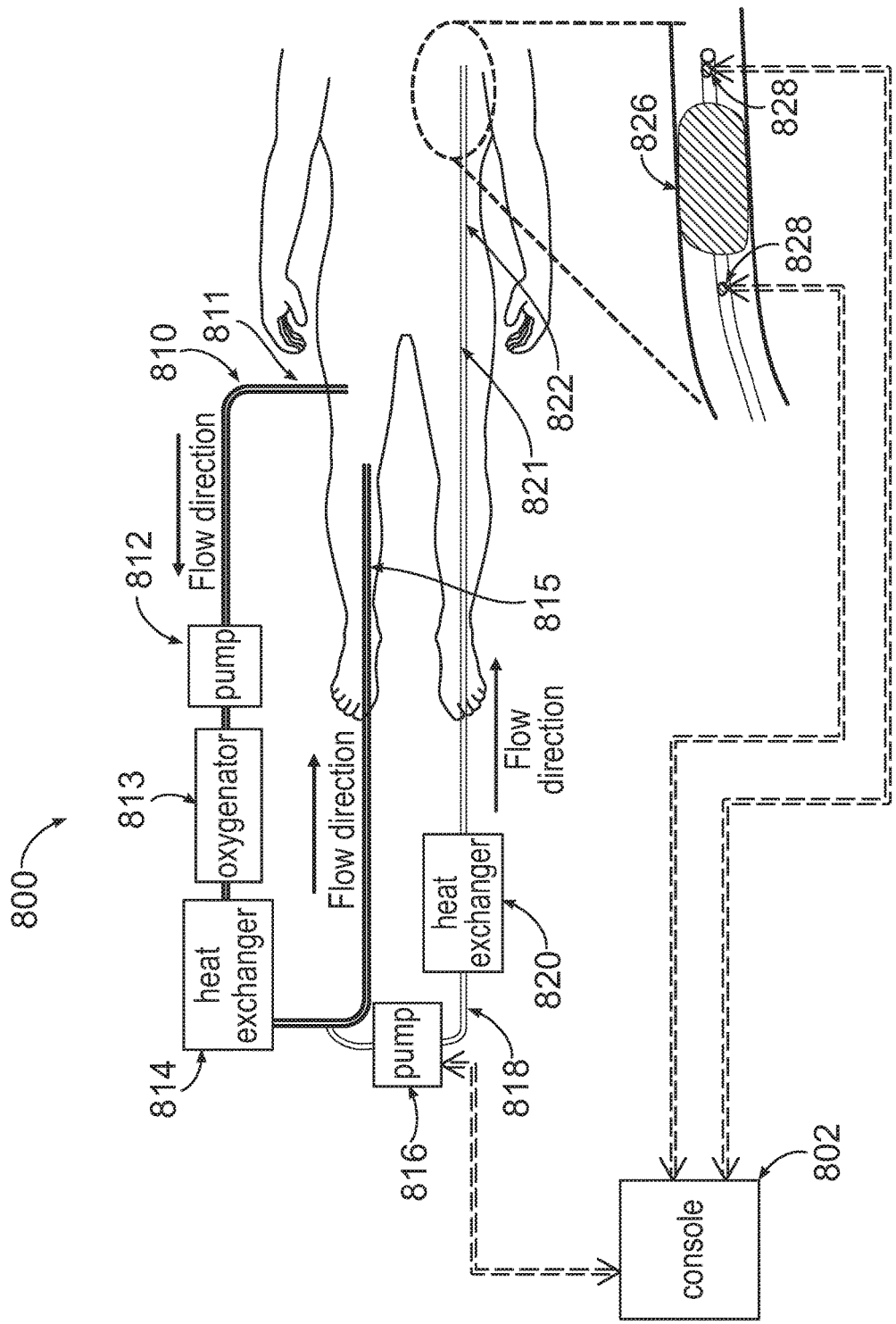
FIG. 8A shows an example extracorporeal circuit system coupled to a console, according to principles of the present disclosure.

FIG. 8A shows an example extracorporeal circuit system 800 coupled to a console 802, according to the principles herein. Similarly to FIG. 7B, the extracorporeal system 800 of FIG. 8A includes a main VA extracorporeal loop 810 that takes blood from the body via a first port 811 and returns it via a second port 815 using a pump 812, an oxygenator 813 and a heat exchanger 814. In a non-limiting example, the oxygenator 813 and heat exchanger 814 can be a combined unit. The example system 800 also include a displacement or volume driven pump 816 located on a branch 818, to pull a controlled volume flow rate of blood out of the main circuit and inject it through an independent heat exchanger 820, a third port 821, and a distal injector member 822 to a local region of a body. Also similarly to the non-limiting example system of FIG. 7B, the injector member includes a imposed minimum conductance component 826 and a pressure sensor pair 828. In the example of FIG. 8A, the console 802 is coupled to the displacement or volume driven pump 816 located on a branch 818 and the pressure sensor pair 828. In other examples, the console 802 can be coupled to different components of the system, including to any one or more of the pumps, heat exchangers, and/or oxygenators of the example system.

The non-limiting example system of FIG. 8A can include temperature sensors coupled to regions of the body to allow provide measurement of temperature at the two independently controlled temperature zones in the body. For example, at least one temperature sensor can be disposed at or otherwise coupled to the region perfused by the second port and at least one temperature sensor can be disposed at or otherwise coupled to the local region of the body perfused by the distal injector member. The at least one temperature sensor disposed at or otherwise coupled to the region perfused by the second port can be configured to measure an average core body temperature and/or average system temperature of a portion of body. The at least one temperature sensor disposed at or otherwise coupled to the local region of the body perfused by the distal injector member configured to measure the temperature of the local region.

In an example, the console 802 can be configured as an operating console. In this example, the operating console can include a water chillers/heaters to drive the heat exchangers and a graphic user interface configured to display user instructions for implementation of operational steps of an operating sequence. The graphic user interface of console 802 can be configured to implement the operating sequence to cause the extracorporeal circuit to control the temperature of the blood perfused by the second port to adjust a temperature measurement reported by at least one temperature sensor to stay within a core body target range, and cause the extracorporeal circuit to control the temperature of the blood injected to the local region such that at least one temperature sensor reports a temperature measurement within a target region temperature range.

The example console 802 can be configured to automate the performance of the Gb and Gtip measurement using the methodology of the controlled flow partitioning system described herein. Based on input received, the console can cause a processor to execute instructions for recording data indicative of the flow inside and values of pressure on the injector member, while also controlling that amount of the injected flow rate, to aid in or enable automatic performance of the methodology of measurement of the proximal and distal conductances at the injector member according to the principles of any of the examples described herein. Such an example console 802 can be configured to automate the controlled flow partitioning system, where it is applied on the injector member coupled to a full extracorporeal loop, or to another catheter system with an extracorporeal volume flow rate source such as, but not limited to, the example in FIG. 6A.

Figure 8B:
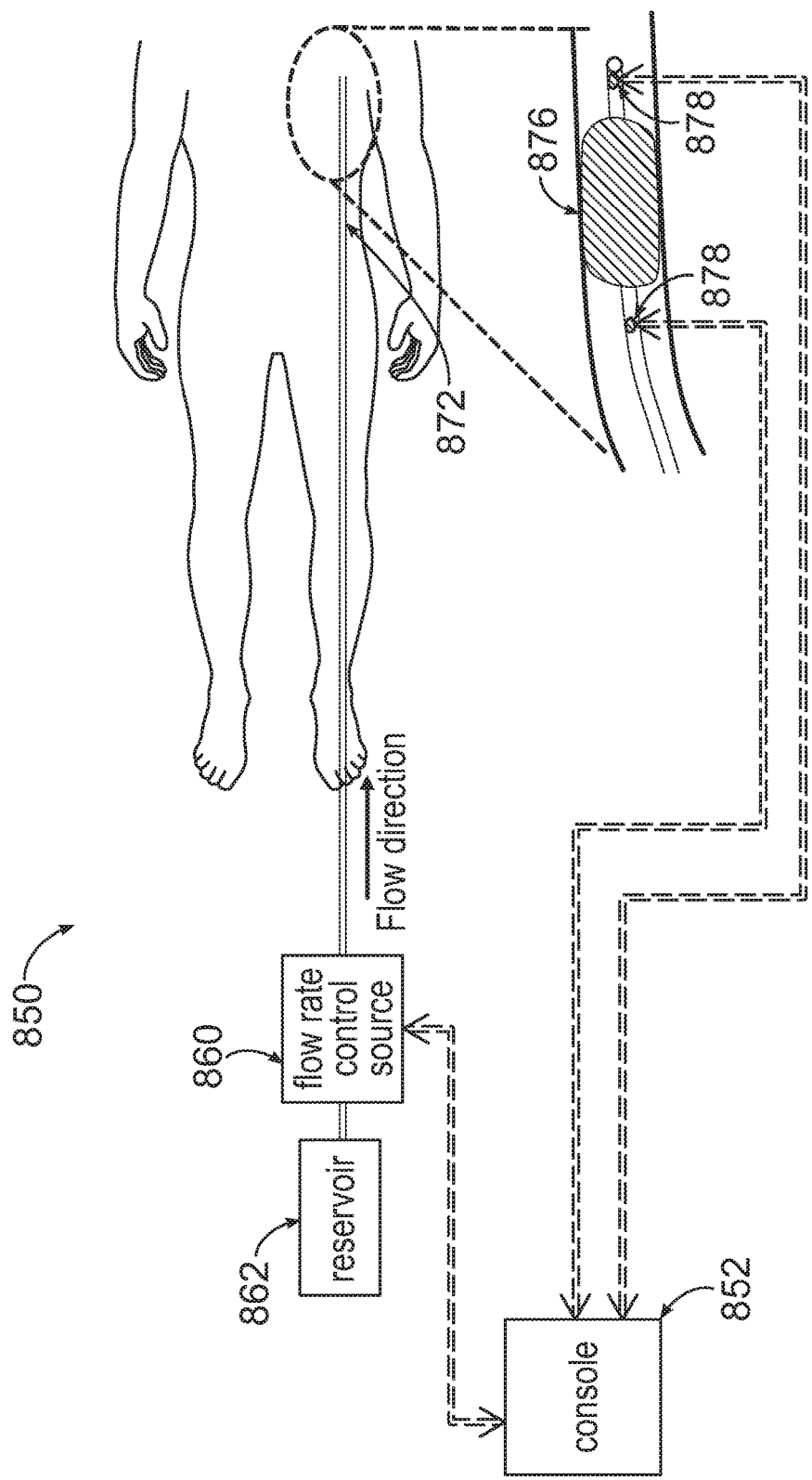
FIG. 8B shows another example extracorporeal circuit system coupled to a console, according to principles of the present disclosure.

FIG. 8B shows another example system 850 coupled to a console 852, according to the principles herein. The example system 850 includes a flow rate control source 860 and reservoir 862. As a non-limiting example, the example flow rate control source 860 and reservoir 862 can be, but is not limited to, a syringe or syringe drive. The example system 850 also includes a distal injector member 872 coupled to a local region of a body. The injector member 872 includes a imposed minimum conductance component 876 and a pressure sensor pair 878. In the example of FIG. 8B, the console 802 is coupled to the flow rate control source 860 and the pressure sensor pair 878. In the example of FIG. 8B, the flow rate control source 860 and reservoir 862 are used to establish the two Ftip settings of the controlled flow partitioning system (according to any of the examples described hereinabove). As a non-limiting example, the settings based on instructions received at the console can be to first withdraw blood to the reservoir at, e.g., 50 ml/min for 2 minutes, then wait two minutes, then return blood at 50 ml/min for two minutes. In this non-limiting example, this establishes Ftip=−50 ml/min, Ftip=0, and Ftip=+50 ml/min Based on input received at the console 852, e.g., from a user or another computing device, instructions can be executed to perform any other desirable procedure according to settings specified in the input.

An example system according to the principles herein can include one or more controllers for controlling a flow of fluid. For example, the one or more controllers can be coupled to an injection member to control the flow of fluid out of the distal tip of the injector member.

Figure 9:
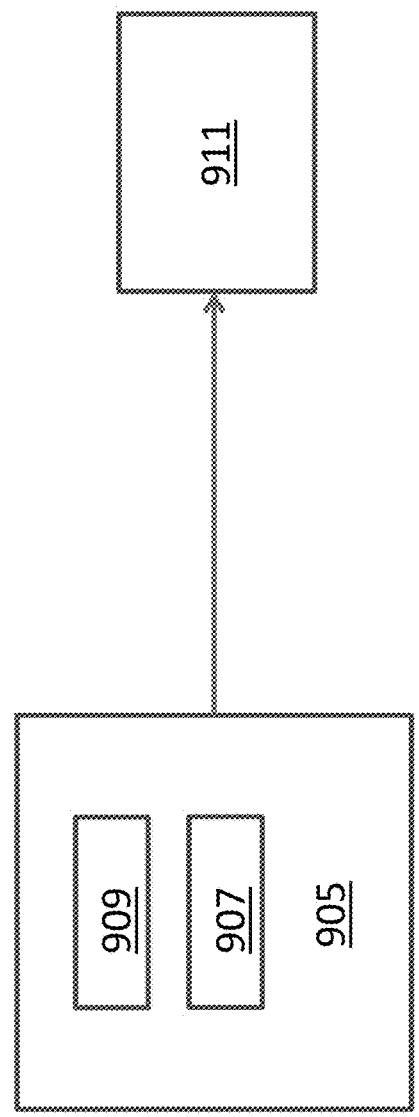
FIG. 9 is a block diagram showing an example computing device, according to principles of the present disclosure.

An example system according to the principles herein can include a console. FIG. 9 shows an example console 905, including at least one processing unit 907 and a memory 909. An example console can include, for example, a desktop computer, a laptop computer, a tablet, a smartphone, a server, a computing cloud, combinations thereof, or any other suitable device or devices capable of electronic communication with a controller or other system according to the principles herein. Example processing unit 907 can include, but is not limited to, a microchip, a processor, a microprocessor, a special purpose processor, an application specific integrated circuit, a microcontroller, a field programmable gate array, any other suitable processor, or combinations thereof. Example memory 909 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof.

In an example, the console can include a display unit 911. Example display unit 111 can include, but is not limited to, a LED monitor, a LCD monitor, a television, a CRT monitor, a touchscreen, a computer monitor, a touchscreen monitor, a screen or display of a mobile device (such as but not limited to, a smartphone, a tablet, or an electronic book), and/or any other display unit.

Figure 10A:
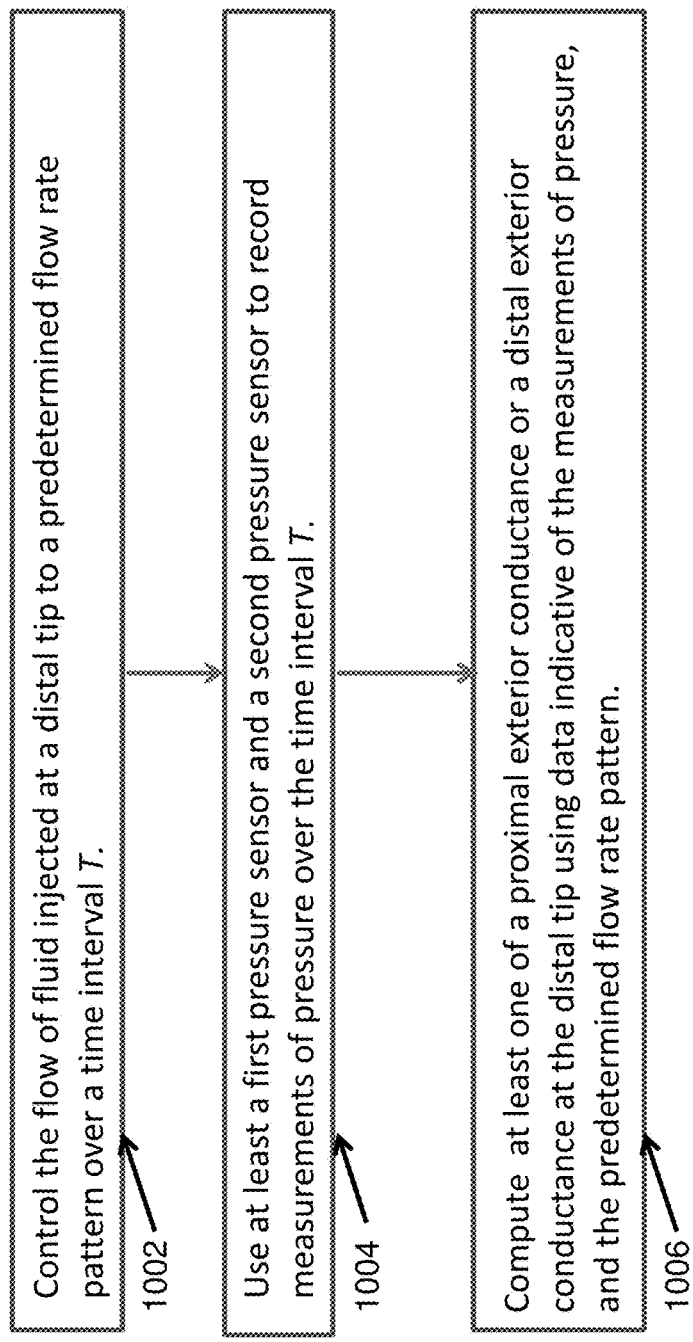
FIGS. 10A-10B show flow diagrams illustrating example methods, according to principles of the present disclosure.
Figure 10B:
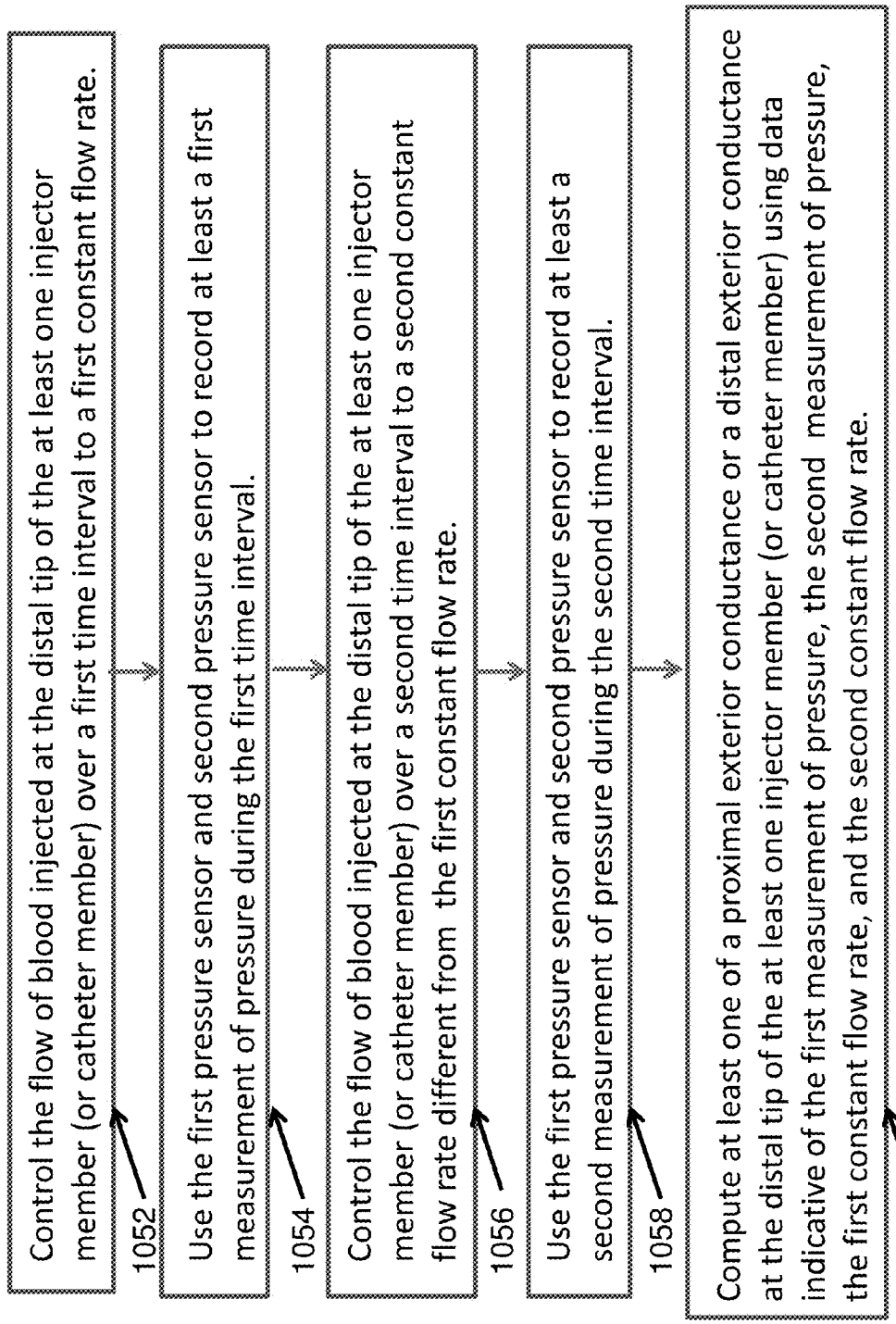

FIGS. 10A-10B show example methods that can be implemented using an example flow partitioning system, or an example system including at least two pressure sensors coupled to a catheter member, according to the principles herein. One of more of the steps of FIGS. 10A-10B can be implemented using a controller based on a command or other signal from a processing unit executing instructions stored to a memory.

FIG. 10A shows an example method that includes (step 1002) controlling the flow of fluid injected at the distal tip of the injector member to a predetermined flow rate pattern over a time interval T, (step 1004) recording measurements of pressure using the first pressure sensor and second pressure sensor over the time interval T, and (step 1006) computing at least one of a proximal exterior conductance or a distal exterior conductance at the distal tip using data indicative of the measurements of pressure, and the predetermined flow rate pattern. The distal tip can be a portion of an injector member of an extracorporeal circuit or a catheter member. In an example, the flow rate pattern can be controlled using an injection flow rate source. In an example, the injection flow rate source can be a pump.

FIG. 10B shows another example method that can be implemented using an example flow partitioning system, or an example system including at least two pressure sensors coupled to a catheter member, according to the principles herein. In step 1052, the flow of blood injected at the distal tip of an injector member (or catheter member) is controlled over a first time interval ($T_A$) to a first constant flow rate. In step 1054, each of the first pressure sensor and the second pressure sensor is used to record at least a first measurement of pressure ($P_{1A}$ and $P_{1B}$) during the first time interval ($T_A$). In step 1056, the flow of blood injected at the distal tip of the injector member is controlled over a second time interval ($T_B$) to a second constant flow rate different from the first constant flow rate. In step 1058, each of the first pressure sensor and the second pressure sensor is used to record at least a second measurement of pressure ($P_{2A}$ and $P_{2B}$) during the second time interval ($T_B$). In step 1060, at least one processor of the processing unit is used to compute at least one of a proximal exterior conductance or a distal exterior conductance at the distal tip of the injector member (or catheter member) using data indicative of the first measurement of pressure, the second measurement of pressure, the first constant flow rate, and the second constant flow rate.

In an example, the example console can cause the display unit to display an indication of the proximal exterior conductance, or the distal exterior conductance, or both, based on the computation.

In an example, the processing unit can also be caused to compute a projection of at least one of a proximal exterior conductance or a distal exterior conductance over a third time interval ($T_C$) later than the first time interval ($T_A$) and the second time interval ($T_B$).

Figure 11:
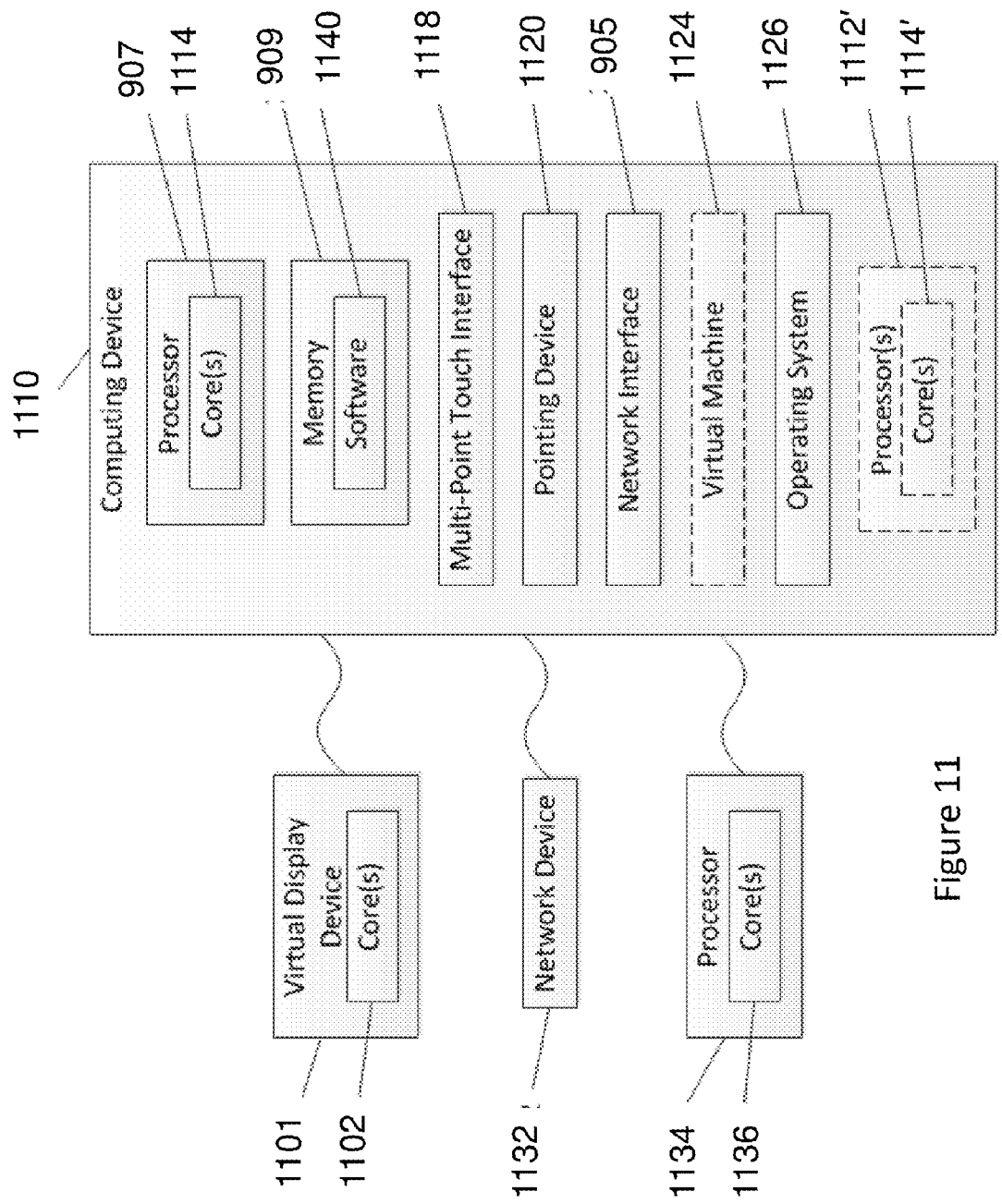
FIG. 11 is an example computational device block diagram, according to principles of the present disclosure.

FIG. 11 is a block diagram of an example computing device 1110 that can be used to implement an operation according to the principles herein. In any example herein, computing device 1110 can be configured as a console. For clarity, FIG. 11 also refers back to and provides greater detail regarding various elements of the example system of FIG. 9. The computing device 1110 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 909 included in the computing device 1110 can store computer-readable and computer-executable instructions or software for performing the operations disclosed herein. For example, the memory 909 can store a software application 1140 which is configured to perform various of the disclosed operations (e.g., causing a controller to control flow, recording a pressure sensor measurement, or performing a computation). The computing device 1110 can also include configurable and/or programmable processor 907 and an associated core 1114, and optionally, one or more additional configurable and/or programmable processing devices, e.g., processor(s) 1112' and associated core(s) 1114' (for example, in the case of computational devices having multiple processors/cores), for executing computer-readable and computer-executable instructions or software stored in the memory 909 and other programs for controlling system hardware. Processor 907 and processor(s) 1112' can each be a single core processor or multiple core (1114 and 1114') processor.

Virtualization can be employed in the computing device 1110 so that infrastructure and resources in the console can be shared dynamically. A virtual machine 1124 can be provided to handle a process running on multiple processors so that the process appears to be using only one computing resource rather than multiple computing resources. Multiple virtual machines can also be used with one processor.

Memory 909 can include a computational device memory or random access memory, such as DRAM, SRAM, EDO RAM, and the like. Memory 909 can include other types of memory as well, or combinations thereof.

A user can interact with the computing device 1110 through a visual display unit 1128, such as a computer monitor, which can display one or more user interfaces 1130 that can be provided in accordance with example systems and methods. The computing device 1110 can include other I/O devices for receiving input from a user, for example, a keyboard or any suitable multi-point touch interface 1118, a pointing device 1120 (e.g., a mouse). The keyboard 1118 and the pointing device 1120 can be coupled to the visual display unit 1128. The computing device 1110 can include other suitable conventional I/O peripherals.

The computing device 1110 can also include one or more storage devices 1134, such as a hard-drive, CD-ROM, or other computer readable media, for storing data and computer-readable instructions and/or software that perform operations disclosed herein. Example storage device 1134 can also store one or more databases for storing any suitable information required to implement example systems and methods. The databases can be updated manually or automatically at any suitable time to add, delete, and/or update one or more items in the databases.

The computing device 1110 can include a network interface 1122 configured to interface via one or more network devices 1132 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1122 can include a built-in network adapter, network interface card, PCMCIA network card, card bus network adapter, wireless network adapter, USB network adapter, modem or any other device suitable for interfacing the computing device 1110 to any type of network capable of communication and performing the operations described herein. Moreover, the computing device 1110 can be any computational device, such as a workstation, desktop computer, server, laptop, handheld computer, tablet computer, or other form of computing or telecommunications device that is capable of communication and that has sufficient processor power and memory capacity to perform the operations described herein.

The computing device 1110 can run any operating system 1126, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 1126 can be run in native mode or emulated mode. In an example, the operating system 1126 can be run on one or more cloud machine instances.

In non-limiting examples, computing device according to the principles herein can include any one or more of a smartphone (such as but not limited to an iPhone®, an Android™ phone, or a Blackberry@), a tablet computer, a laptop, a slate computer, an electronic gaming system (such as but not limited to an XBOX®, a Playstation®, or a Wii®), an electronic reader (an e-reader), and/or other electronic reader or hand-held computing device.

In any example herein, at least one method herein can be implemented using a computer program. The computer program, also known as a program, software, software application, script, application or code, can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

An example computing device can include an application (an "App") to perform such functionalities as analyzing the temperature sensor data, pressure sensor data and computing the conductance, as described herein. As a non-limiting example, the App can be configured for download as a *.apk file for an Android™ compatible system, or as a *.app file for an iOS® compatible system.

An example console according to the principles herein can be used to implement a control procedure for an operational sequence, such as described in international (PCT) Application No. PCT/US2015/033529, which is incorporated herein by reference. For example, the console can includes a display including a user interface, and chillers/heaters to drive the heat exchangers. The example console can be coupled to at least one first temperature sensor positioned to measure an average core body temperature and/or average system temperature of a portion of body perfused using the second port, and at least one second temperature sensor positioned to measure the temperature of a local region perfused by the injector member. The user interface configured to display user instructions for implementation of operational steps of an operating sequence. A non-limiting example console can include a user interface and computing device as defined herein to implement a semi-automated control procedure such that, in all phases of an operation, temperature bands can be set in the apparatus and the system can alert the operator to adjust the chiller temperatures if the sensor temperatures drift out of target bounds during each phase. A non-limiting example console can include a user interface and computing device as defined herein to implement a fully automated control procedure such that, in all phases of an operation, temperature bands can be set in the apparatus and the system can be configured to automatically adjust the chiller temperatures if the sensor temperatures drift out of target bounds during each phase.

Any example system and method herein can be used to establish and control two different temperature zones of at least portions of a body for at least portions of a treatment procedure for a patient that suffered a local or global ischemic insult or circulation damage, such as described in international (PCT) Application No. PCT/US2015/033529. An example method can include coupling a systemic perfusion extracorporeal circuit (SPEC) to the body using a peripheral placed loop and coupling a local perfusion extracorporeal circuit (LPEC) to blood flowing within the vasculature to a local target region of the body (such as but not limited to the brain). The SPEC can includes a SPEC input flow port and a SPEC output flow port to be in contact with blood flowing within the vasculature, a SPEC pump, and a SPEC heat exchanger. The LPEC can include a LPEC input flow port and a LPEC output flow port in contact with blood flowing within the vasculature, a LPEC pump, and a LPEC heat exchanger. The LPEC input flow port is disposed to perfuse the local target region of the body. The method includes positioning at least one SPEC sensor to measure the average core body temperature and/or average system temperature of the body perfused by the SPEC, positioning at least one LPEC sensor to measure the temperature of the local target region perfused by the LPEC, performing operational steps of at least a minimum operating sequence, and implementing a control procedure to record measurements of the at least one LPEC sensor and at least one SPEC sensor and to control independently a rate of blood flow and a heat exchanger temperature of the SPEC and LPEC, respectively. The LPEC can include an injector member including a distal tip, disposed to be in contact with blood flowing within the vasculature, where the LPEC injector member is disposed to perfuse the local target region of the body. The LPEC can include an imposed minimum conductance component, or a controlled flow partitioning system, or both, according to the principled described herein. In an example where the LPEC includes a controlled flow partitioning system, the LPEC pump can serve as an injection flow rate source for the controlled flow partitioning system.

The LPEC input flow port can be disposed in contact with either the left common carotid artery, right common carotid artery, or an artery downstream of one of those locations.

In an example, the control procedure can cause the SPEC to control the temperature of the blood injected by the SPEC to adjust the temperature measurement reported by the SPEC temperature sensors to stay within a target core body temperature range, and cause the LPEC to control the temperature of the blood injected to the target region such that the one or more LPEC temperature sensors report a temperature measurement according to a specified pattern of target region temperature values. The SPEC temperature sensors can be one or more of a bladder temperature sensor or a rectal temperature sensor.

In another example, the control procedure can cause the SPEC to adjust the systemic temperature of the body such that the one or more SPEC temperature sensors indicate an average temperature within the range from about 32° C. to less than about 37° C., and cause the LPEC to control the temperature of the blood to the target region such that the one or more LPEC temperature sensors indicate a temperature below about 30° C. The control procedure can cause the SPEC to increase the temperature of the blood to prevent the average temperature from falling below about 32° C. The control procedure can cause the LPEC to cool the temperature of the blood to a value within the range of about 10° C. to about 30° C.

Any example system herein can include a control system programmed to execute the control procedure. For example, the control system can be programmed to set a flow rate and a temperature at the LPEC pump and LPEC heat exchanger independently from a flow rate at the SPEC pump. The control system can be programmed to cause the LPEC to control the temperature of the blood to the target region automatically, or based on a manual input. The control system can be programmed to cause the SPEC to increase the temperature of the blood to prevent the average temperature from falling below about 32° C. The control system can be programmed to cause the LPEC to cool the temperature of the blood to a value within the range of about 10° C. to about 30° C.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, one or more floppy disks, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:
   coupling an extracorporeal circuit to a portion of a body of a patient, the extracorporeal circuit comprising:
      a flow port to return blood from the extracorporeal circuit to a vasculature at a region of the body;
      an injector member coupled to the flow port, the injector member comprising a distal tip and a shaft having a lumen;
      a controlled partitioning flow system, the system comprising:
         at least a first pressure sensor disposed proximate to the distal tip;
         at least a second pressure sensor disposed on an outer surface of the shaft of the injector member; and
         an injection flow rate source coupled to the injection member to control a flow of fluid injected at the distal tip of the injector member;
   controlling the flow of fluid injected at the distal tip of the injector member, using the injection flow rate source, to a predetermined flow rate pattern over a time interval T;
   recording measurements of pressure using the first pressure sensor and second pressure sensor over the time interval T; and
   computing at least one of a proximal exterior conductance or a distal exterior conductance at the distal tip of the injector member using data indicative of the measurements of pressure, and the predetermined flow rate pattern.

2. The method of claim 1, wherein the predetermined flow rate pattern comprises a first constant flow rate over a first time interval $t_1 < T$, and a second constant flow rate different from the first constant flow rate over a second time interval $t_2 < T$ subsequent to the first time interval.

3. The method of claim 2, wherein the controlling the flow of fluid comprises:
   controlling the flow of fluid injected at the distal tip of the injector member, using the injection flow rate source, over the first time interval $t_1$ to the first constant flow rate; and
   controlling the flow of fluid injected at the distal tip of the injector member, using the injection flow rate source, over the second time interval $t_2$ to the second constant flow rate.

4. The method of claim 3, wherein the recording the measurements of pressure comprises:
   recording first measurements of pressure over the first time interval $t_1$ using the first pressure sensor and the second pressure sensor; and
   recording second measurements of pressure over the second time interval $t_2$ using the first pressure sensor and the second pressure sensor.

5. The method of claim 4, wherein the at least one of the proximal exterior conductance or the distal exterior conductance at the distal tip of the injector member is computed using data indicative of the first measurements of pressure, the second measurements of pressure, the first constant flow rate, and the second constant flow rate.

6. The method of claim 1, wherein the second pressure sensor is disposed on the outer surface of the shaft of the injector member at a distance greater than or approximately equal to about twice a diameter of the vasculature proximal from the distal tip.

7. The method of claim 1, further comprising controlling the flow of fluid injected at the distal tip of the injector member to maintain a flow rate at a value such that a region of the vasculature proximate to an imposed minimum conductance component is flushed with blood flow.

8. The method of claim 1, further comprising controlling the flow such that fluid injected at the distal tip flows according to a step function.

9. The method of claim 1, wherein the second pressure sensor is disposed at a distance greater than about 1.0 cm proximal from the distal tip.

10. The method of claim 1, further comprising adding an amount of at least one of a drug or pharmacological agent to a fluid injected through the injector member.

11. The method of claim 10, further comprising adjusting a concentration of the at least one of drug or pharmacological agent using the measurements of pressure using the first pressure sensor and second pressure sensor and a measured proximal exterior conductance to produce a desired concentration of the at least one of drug or pharmacological agent in a mixed distal flow.

* * * * *